US006610660B1

(12) United States Patent
Saavedra et al.

(10) Patent No.: US 6,610,660 B1
(45) Date of Patent: Aug. 26, 2003

(54) $O^2$-ARYLATED OR $O^2$-GLYCOSYLATED 1-SUBSTITUTED DIAZEN-1-IUM-1,2-DIOLATES AND $O^2$-SUBSTITUTED 1-[(2-CARBOXYLATO) PYRROLIDIN-1-YL] DIAZEN-1-IUM-1,2-DIOLATES

(75) Inventors: Joseph E. Saavedra, Thurmount, MD (US); Larry K. Keefer, Bethesda, MD (US); Aloka Srinivasan, Wilmington, DE (US); William G. Rice, Frederick, MD (US); Xinhua Ji, Gaithersburg, MD (US); Christian Bogdan, Wasserturmstrasse (DE)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/254,301

(22) PCT Filed: Sep. 26, 1997

(86) PCT No.: PCT/US97/17267

§ 371 (c)(1),
(2), (4) Date: May 3, 1999

(87) PCT Pub. No.: WO98/13358

PCT Pub. Date: Apr. 2, 1998

Related U.S. Application Data

(60) Provisional application No. 60/051,696, filed on Jul. 3, 1997, provisional application No. 60/045,917, filed on May 7, 1997, and provisional application No. 60/026,816, filed on Sep. 27, 1996.

(51) Int. Cl.[7] ..................... C07D 295/22; A61K 31/15; A61P 35/00
(52) U.S. Cl. ..................... 514/25; 514/150; 534/556
(58) Field of Search ..................... 514/25, 149, 44, 514/45, 46, 49, 50, 150; 532/556; 534/556

(56) References Cited

U.S. PATENT DOCUMENTS

| 3,153,094 A | 10/1964 | Reilly et al. |
| 4,954,526 A | 9/1990 | Keefer |
| 5,039,705 A | 8/1991 | Keefer et al. |
| 5,155,137 A | 10/1992 | Keefer et al. |
| 5,208,233 A | 5/1993 | Keefer et al. |
| 5,212,204 A * | 5/1993 | Keefer et al. ............... 514/647 |
| 5,250,550 A | 10/1993 | Keefer et al. |
| 5,366,997 A | 11/1994 | Keefer et al. |
| 5,389,675 A | 2/1995 | Christodoulou et al. |
| 5,405,919 A | 4/1995 | Keefer et al. |
| 5,525,357 A | 6/1996 | Keefer et al. |
| 5,632,981 A | 5/1997 | Saavedra et al. |
| 5,691,423 A | 11/1997 | Smith et al. |
| 5,721,365 A | 2/1998 | Keefer et al. |
| 5,814,656 A * | 9/1998 | Saavedra et al. ........... 514/426 |

FOREIGN PATENT DOCUMENTS

| WO | WO 93 07114 | 4/1993 |
| WO | WO 96 40665 | 12/1996 |

OTHER PUBLICATIONS

Hawley, Gessner, "The Condensed Chemical Dictonary", 1977, Van Nostrand, New York, p. 76.*
Bauer, J.A. et al, "Nitric Oxide Donors: Biochemical Pharmacology and Therapeutics", in Advamces in Pharmacology, vol. 34, 1995, pp. 361–381.*
Saavedra, Joseph E.; Dunams, Tambra M.; Flippen–Anderson, Judith L.; Keefer, Larry K., J. Org. Chem., 57(23), 6134–8 (English) 1992.*
Aebischer et al., *Journal Chem, Soc. Perkin Trans. I*, 2139–2147 (1982).
Gattavecchia et al., *Journal Chem. Soc. Perkin Trans. II*, 689–693 (1986).
Ji et al., *Biochemistry 32* (49), 12949–12954 (1993).
Ji et al., *Biochemistry 36* 9690–9702 (1997).
Kelley et al., *Biochem Journal 304*, 843–848 (1994).
Khodot et al., *Russian Chemical Bulletin 44* (11), 2183–2185 (1995).
Morgan et al., *Cancer Chemother. Pharmacology 37*, 363–370 (1996).
Rice et al., *PNAS 89*, 7703–7707 (1992).
Saavedra et al., *Journal of Medicinal Chemistry 31*, 4361–4365 (1996).

* cited by examiner

Primary Examiner—Mukund J. Shah
Assistant Examiner—Thomas McKenzie
(74) Attorney, Agent, or Firm—Leydig, Voit & Mayer, Ltd.

(57) ABSTRACT

Diazeniumdiolates, wherein the $N^1$ position is substituted by an inorganic or organic moiety and the $O^2$-oxygen is bound to a substituted or unsubstituted aromatic group, are provided. Also provided are $O^2$-glycosylated 1-substituted diazen-1-ium-1,2-diolates ($O^2$-glycosylated diazeniumdiolates) and $O^2$-substituted 1-[(2-carboxylato) pyrrolidin-1-yl]diazen-1-ium-1,2-diolates (1-[(2-carboxylato)pyrrolidin-1-yl]diazeniumdiolates). The $O^2$-aryl diazeniumdiolates are stable with respect to the hydrolytic generation of nitric oxide in neutral to acidic solutions and generate nitric oxide in basic or nucleophilic environments or microenvironments. Also provided are compositions, including pharmaceutical compositions, comprising such compounds and methods of using such compounds.

39 Claims, 2 Drawing Sheets

O²-ARYLATED OR O²-GLYCOSYLATED 1-SUBSTITUTED DIAZEN-1-IUM-1,2-DIOLATES AND O²-SUBSTITUTED 1-[(2-CARBOXYLATO) PYRROLIDIN-1-YL] DIAZEN-1-IUM-1,2-DIOLATES

This application claim benefit to provisional application No. 60/026,816 Sep. 27, 1996 which claims benefit of 60/045,917 May 7, 1997 which claims benefit of 60/051,696 Jul. 3, 1997.

TECHNICAL FIELD OF THE INVENTION

The present invention relates to O²-aryl 1-substituted diazen-1-ium-1,2-diolates (O²-aryl diazeniumdiolates) O²-glycosylated 1-substituted diazeniumdiolates, and O²-substituted 1-[(2-carboxylato)pyrrolidin-1-yl] diazeniumdiolates, compositions comprising such diazeniumdiolates, methods of using such diazeniumdiolates, and methods of preparing O²-aryl diazeniumdiolates.

BACKGROUND OF THE INVENTION

Nitric oxide (NO) has been implicated in a wide variety of bioregulatory processes, and compounds, which contain nitric oxide or are capable of releasing nitric oxide, have been identified as useful in regulating these processes. Many classes of nitric oxide-containing and/or -releasing adducts are known in the art, such as glyceryl trinitrate and nitroprusside (reviewed in U.S. Pat. No. 5,405,919 (Keefer et al.), including limitations of their use in biological applications). The limited utility of such compounds has, in part, given rise to the development of another class of nitric oxide-generating compounds, diazeniumdiolates, which are especially useful biologically.

Diazeniumdiolates include compounds containing an $N_2O_2^-$ functional group and are structurally and functionally distinct from nitrosamines (see, e.g., Reilly, U.S. Pat. No. 3,153,094). The known diazeniumdiolates are disclosed in recently issued patents. U.S. Pat. Nos. 5,039,705 (Keefer et al.) and 5,208,233 (Keefer et al.) disclose secondary amine-nitric oxide adducts and salts thereof. U.S. Pat. Nos. 5,155,137 (Keefer et al.) and 5,250,550 (Keefer et al.) disclose complexes of nitric oxide and polyamines. U.S. Pat. No. 5,389,675 (Christodoulou et al.) discloses mixed ligand metal complexes of nitric oxide-nucleophile adducts and U.S. Pat. Nos. 5,525,357 (Keefer et al.) and 5,405,919 (Keefer et al.) disclose polymer-bound nitric oxide/nucleophile adduct compositions. U.S. Pat. Nos. 4,954,526 (Keefer et al.; the '526 patent) and 5,212,204 (Keefer et al.) disclose the use of ionic diazeniumdiolates as cardiovascular agents. In addition, the '526 patent discloses O²-substituted and metal-bound diazeniumdiolates. Keefer et al., U.S. Pat. No. 5,366,997 ('997), discloses diazeniumdiolates having the formula:

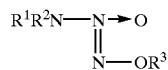

in which the O²-oxygen of the $N_2O_2^-$ group is bonded to the functional group $R^3$. When the $R^3$ group is cleaved from the O²-oxygen, NO can be released spontaneously.

Although Keefer et al. ('997) discloses that (i) $R^1$ and $R^2$, together with the nitrogen atom to which they are bonded, can form a pyrrolidinyl, piperazino or other heterocyclic group, (ii) $R^3$ is a $C_{1-12}$ straight-chain or $C_{3-12}$ branched-chain alkyl, optionally olefinic and/or substituted with hydroxy, halo, acyloxy or alkoxy, a $C_{1-12}$ unsubstituted/substituted acyl, sulfonyl, carboxamido, sulfinyl, sulfenyl, a carbonate derivative or a carbamate derivative, and (iii) the pyrrolidinyl group can have the structure:

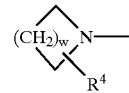

wherein w=4, and $R^4$=hydrogen, a $C_{1-8}$ straight or branched chain alkyl, a $C_{3-6}$ cycloalkyl, or a substituted or an unsubstituted aryl, Keefer et al. ('997) does not disclose that $R^3$ is an aryl or a substituted aryl or that the pyrrolidino group can be substituted with a substituted or unsubstituted carboxyl group (see, also, Example 1 of U.S. Pat. No. 5,632,981) at position 2. Similarly, Keefer et al. ('997) does not disclose O²-glycosylation of diazeniumdiolates.

Heretofore it was not known that O²-aryl substitutions of the diazeniumdiolates was possible. Further, chemical studies of previously disclosed diazeniumdiolates led to the conclusion that they are generally at least as stable at high pH as they are at low pH, and that, unlike certain other classes of "nitrovasodilator" drugs, their rates of NO release are not affected by the presence of nucleophilic thiols.

Thus, there remains a need for such classes of diazeniumdiolates, which offer advantages over other currently available diazeniumdiolates. In this regard, the O²-aryl substituted diazeniumdiolates are advantageous in that they can release NO spontaneously under alkaline conditions or after nucleophilic attack. O²-Aryl substituted diazeniumdiolates also can release NO spontaneously after a combination of oxidative or electophilic activation and nucleophilic attack.

It is, therefore, a principal object of the present invention to provide a nitric oxide/nucleophile adduct in which the O²-oxygen of the $N_2O_2^-$ group is derivatized with an aryl or substituted aryl group to protect the diazeniumdiolate against the spontaneous release of NO. It is another object of the invention to provide a novel class of diazeniumdiolates, which resists releasing nitric oxide in neutral or acidic solutions, but releases NO on nucleophilic attack or on increasing the pH. It is still another object of the present invention to provide O²-glycosylated 1-substituted diazen-1-ium-1,2-diolates and O²-substituted 1-[(2-carboxylato)pyrrolidin-1-yl]diazen-1-ium-1,2-diolates. It is a further object of the present invention to provide compositions comprising such compounds, including compositions comprising a nitric oxide/nucleophile adduct comprising a novel targeting moiety. It is a related object to provide O²-aryl substituted diazeniumdiolates, which are amenable to biological tissue-targeting strategies, which offer greater flexibility and specificity for targeting NO release. It is a still further object of the present invention to provide methods of using such compounds. These and other objects of the present invention, as well as additional inventive features, will be apparent from the description of the invention provided herein.

BRIEF SUMMARY OF THE INVENTION

The present invention provides an $O^2$-aryl substituted diazeniumdiolate (i.e., $O^2$-aryl diazeniumdiolate) illustrated by the formula:

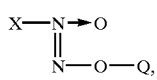
(I)

wherein X is an inorganic or organic moiety and Q is an aryl moiety. In this novel class of compounds an atom of the aryl ring moiety Q is bonded to the $O^2$-oxygen of the $N_2O_2^-$ functional group. The diazeniumdiolates of Formula (I) are stable with respect to the hydrolytic generation of nitric oxide in neutral to acidic solutions. Surprisingly, these novel compounds, or the resultant product of these compounds after oxidative or electrophilic activation, have proven capable of generating nitric oxide in basic or nucleophilic environments, in which the aryl moiety is separated from the remainder of the diazeniumdiolate.

The present invention also provides $O^2$-glycosylated 1-substituted diazen-1-ium-1,2-diolates and $O^2$-substituted 1-[(2-carboxylato)pyrrolidin-1-yl]diazen-1-ium-1,2-diolates, both of which can be represented by the formula:

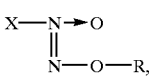
(Ia)

in which X and R are organic and/or inorganic moieties as defined herein, although for $O^2$-glycosylated diazeniumdiolates, R must be a saccharide.

Further with respect to the $O^2$-glycosylated 1-substituted diazen-1-ium-1,2-diolates, the moiety X can be any organic or inorganic group. Preferably, X contains atoms other than carbon and hydrogen, and is linked to the nitrogen of the diazeniumdiolate through an atom other than carbon. Most preferably, X is an amino group, and is linked to the nitrogen of the diazeniumdiolate through a nitrogen atom.

With respect to the $O^2$-substituted 1-[(2-carboxylato)pyrrolidin-1-yl]diazen-1-ium-1,2-diolates, X of Formula Ia can be

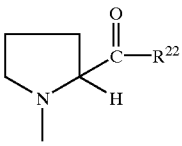

such that the [1-(2-carboxylato)pyrrolidin-1-yl] diazeniumdiolates can be structurally represented by the formula:

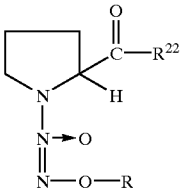

wherein $R^{22}$ is hydrogen, hydroxyl, OM, wherein M is a cation, halo, or $X^1R^{23}R^{24}$, wherein $X^1$ is oxygen, nitrogen or sulfur and $R^{23}$ and $R^{24}$ are independently a substituted or unsubstituted $C_{1-24}$ alkyl, a substituted or unsubstituted $C_{3-24}$ cycloalkyl, a substituted or unsubstituted $C_{2-24}$ olefinic, a substituted or unsubstituted aryl (such as acridine, anthracene, benzene, benzofuran, benzothiophene, benzoxazole, benzopyrazole, benzothiazole, carbazole, chlorophyll, cinnoline, furan, imidazole, indole, isobenzofuran, isoindole, isoxazole, isothiazole, isoquinoline, naphthalene, oxazole, phenanthrene, phenanthridine, phenothiazine, phenoxazine, phthalimide, phthalazine, phthalocyanine, porphin, pteridine, purine, pyrazine, pyrazole, pyridazine, pyridine, pyrimidine, pyrrocoline, pyrrole, quinolizinium ion, quinoline, quinoxaline, quinazoline, sydnone, tetrazole, thiazole, thiophene, thyroxine, triazine, and triazole), or a heterocyclic group, such as glycosyl, and the like, and when $X^1$ is O or S, there is no $R^{24}$ group. Alternatively, when $X^1$ is nitrogen, $R^{23}$ and $R^{24}$, together with $X^1$, form a heterocyclic ring, such as a heterocyclic ring selected from the group consisting of:

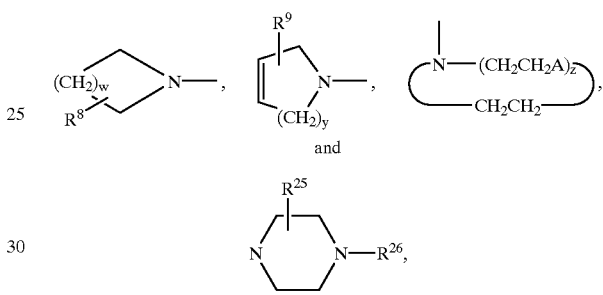

and in which A is N, O, or S, w is 1–12, y is 1 or 2, z is 1–5, $R^8$, $R^9$, $R^{25}$, and $R^{26}$ are hydrogen, a $C_{1-8}$ straight chain alkyl, a $C_{3-8}$ branched chain alkyl, a $C_{3-8}$ cycloalkyl, or an aryl. The aforementioned $R^{23}$ and $R^{24}$ groups can be unsubstituted or substituted as appropriate. For example, the $R^{23}$ and $R^{24}$ groups can be substituted as appropriate with acyloxy, acylthio, hydroxyl, amino, carboxyl, mercapto, halo, amido, sulfonyl, sulfoxy, sulfenyl, phosphono, phosphate, and the like.

Further with respect to the $O^2$-substituted 1-[(2-carboxylato)pyrrolidin-1-yl]diazen-1-ium-1,2-diolates, the moiety R of Formula Ia can be any organic or inorganic moiety, which is covalently bound to the terminal oxygen of the diazeniumdiolate as shown but which is other than hydrogen and is a substituted or unsubstituted $C_{1-12}$ straight chain or $C_{3-12}$ branched chain alkyl, a substituted or unsubstituted $C_{2-12}$ straight chain or $C_{3-12}$ branched chain olefinic, a substituted or unsubstituted $C_{1-12}$ acyl, sulfonyl, carboxamido, a glycosyl group, an aryl group, or a group of the formula $—(CH_2)_n—ON=N(O)NR^{28}R^{29}$, wherein n is an integer of 2–8, and $R^{28}$ and $R^{29}$ are independently a $C_{1-12}$ straight chain alkyl, a $C_{3-12}$ branched chain alkyl, a $C_{2-12}$ straight chain or $C_{3-12}$ branched chain olefinic, or $R^{28}$ and $R^{29}$, together with the nitrogen atom to which they are bonded, form a heterocyclic group, preferably a pyrrolidino, piperidino, piperazino or morpholino group. The aforementioned R groups can be unsubstituted or substituted. Preferred substitutions include those made with hydroxy, halo, acyloxy, alkoxy, acylthio, or benzyl.

In another aspect, the present invention comprises a composition, including a pharmaceutical composition, comprising a present inventive diazeniumdiolate. The pharmaceutical composition preferably additionally comprises a pharmaceutically acceptable carrier.

In yet another aspect, the present invention provides methods of using a compound in accordance with the present invention.

In still another aspect, the present invention provides a method of making $O^2$-aryl diazeniumdiolates.

Figure 1:
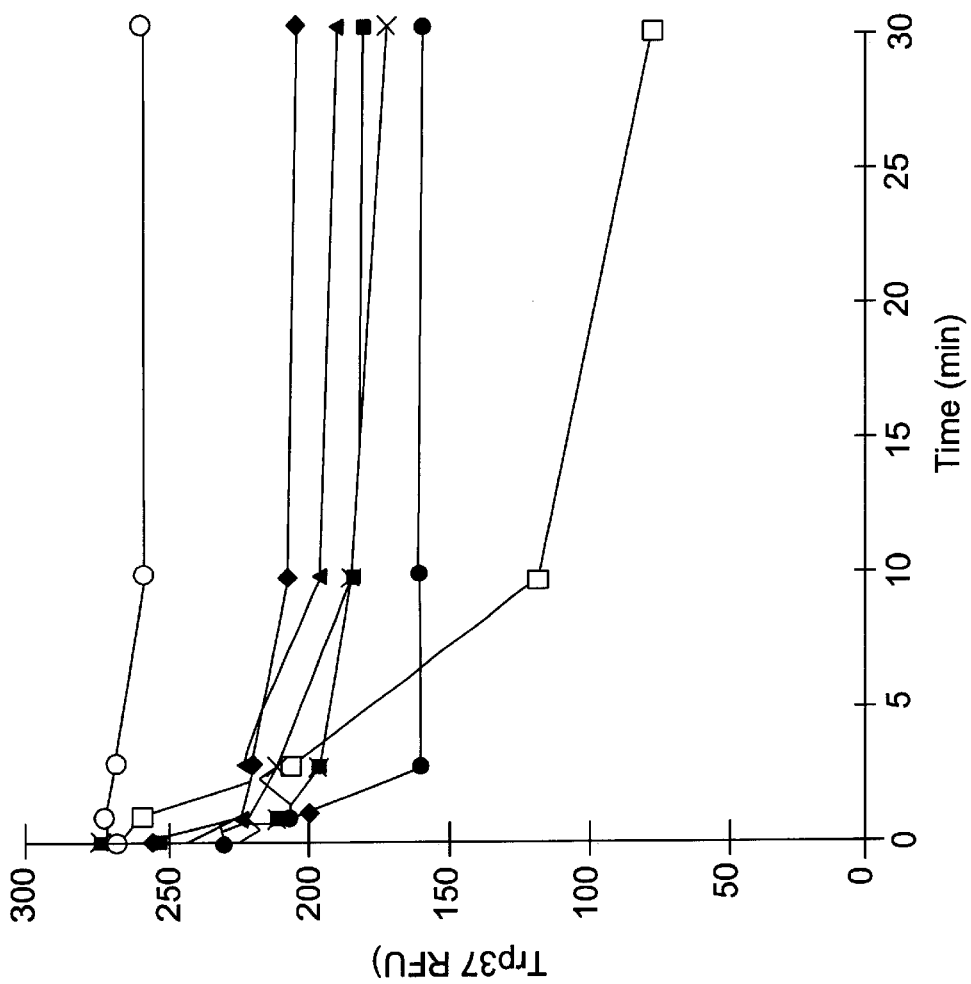
FIG. 1 is a graph of Trp37 fluorescence (RFU) versus time (min), which depicts zinc ejection from HIV-1 nucleocapsid p7 protein by $O^2$-aryl diazeniumdiolates. In the graph, ○ represents the negative control, i.e., no drug, □ represents the positive control, i.e., 624151 (See Rice et al., *Antimicrob. Agents Chemother.* 41: 419426 (1997)), ■ represents the compound of Example 1 (LK1), ♦ represents the compound of Example 8 (LK2), ▲ represents the compound of Example 5 (LK3), ● represents the compound of Example 10 (LK4), and X represents the compound of Example 11 (LK5).
Figure 2:
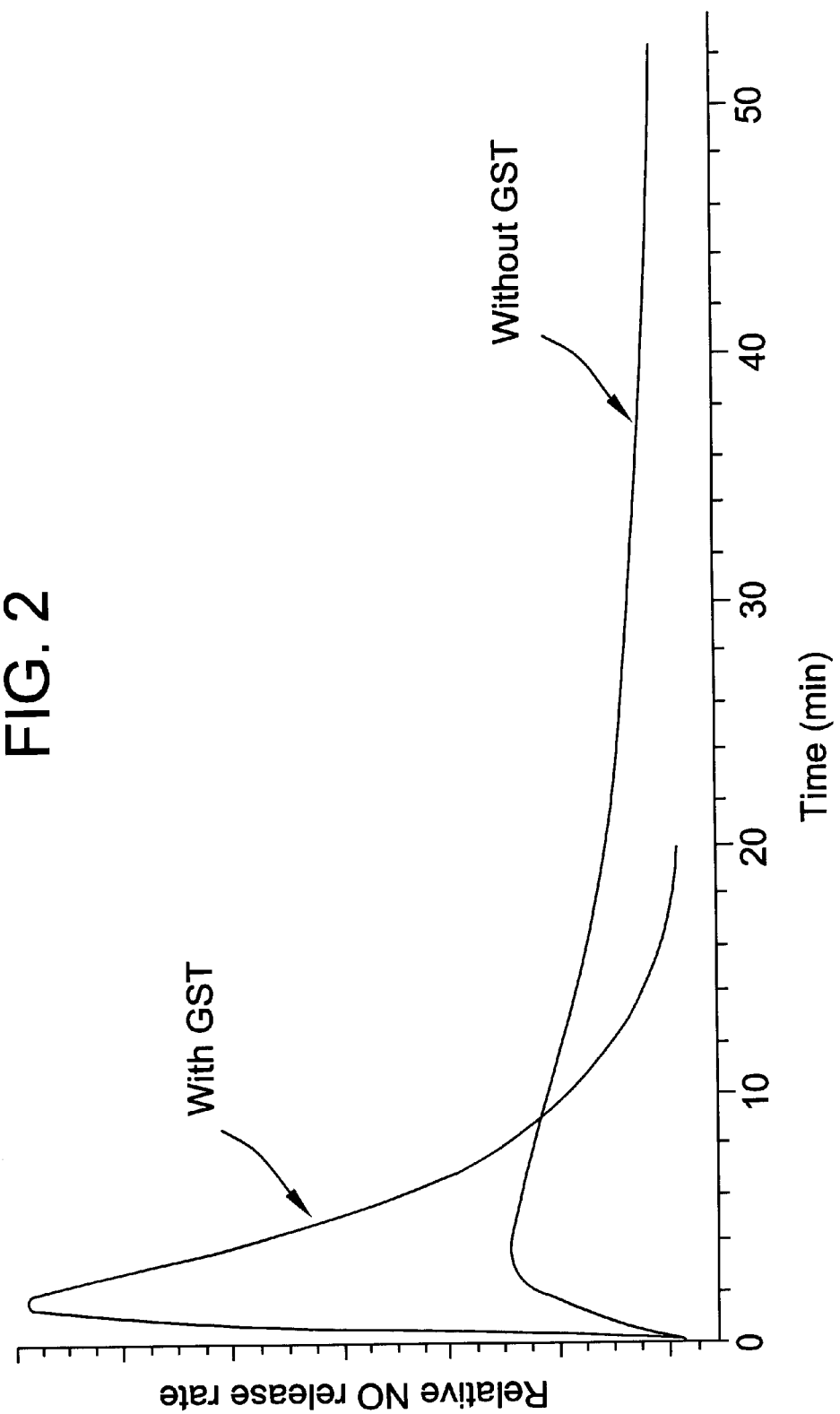
FIG. 2 is a graph of relative NO release rate versus time (min), which depicts the catalysis of NO release from DNP-PYRRO/NO by glutathione S-transferase (GST).

DETAILED DESCRIPTION OF THE INVENTION $O^2$-arylated diazeniumdiolates

The present invention provides an $O^2$-aryl 1-substituted diazeniumdiolate (i.e., $O^2$-aryl 1-substituted diazen-1-ium-1,2-diolate) having the formula:

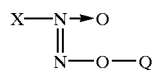

(I)

wherein X is an organic or inorganic moiety and Q is an aryl group.

In accordance with the invention, the $O^2$-oxygen of the $N_2O_2^-$ group is bonded directly to an atom of the ring of the aryl group. Stated another way, there are no spacer atoms (e.g., methylene) that separate the $O^2$-oxygen from the aryl ring. If the aryl group comprises a bicyclic or polycyclic moiety and all rings of the aryl group are not aromatic, then the linkage between the $O^2$-oxygen and the aryl group is through an atom that is part of an aromatic ring. Further, the $O^2$-oxygen can be linked to any aromatic, ring atom of the aryl group that is capable of bonding to the $O^2$-oxygen of the $N_2O_2^-$ group. Atoms of the aromatic ring that are capable of bonding with the $O^2$-oxygen of the $N_2O_2^-$ group are typically carbon and nitrogen, although there can be other linkages as well.

While not wishing to be bound to any particular theory, it is presently believed that the bonding of the $O^2$-oxygen with the atom of the aryl ring is accomplished by bonding to an activated atom of the ring. Activation can be accomplished through any suitable mechanism. In this regard, a preferred mechanism of activating an aryl ring is by reacting the diazeniumdiolate through an atom of the aryl ring possessing a partial positive charge or, more specifically, by displacing an amino substituent of the ring structure.

In the first preferred reaction mechanism, the aryl ring is substituted by a suitable electron-withdrawing group(s), which can be part of the ring, as in Example 12, and a "leaving group" prior to reaction with the diazeniumdiolate. It will be appreciated by those skilled in the art that the electron-withdrawing group and the leaving group can, in some instances, be the same moiety. The leaving group is displaced by the diazeniumdiolate to form the $O^2$-aryl diazeniumdiolate of the present invention. Suitable leaving groups include, but are not limited to, F, Cl, Br, I, $NO_2$, $OSO_2R$, and $OSO_3R$, wherein R is an organic moiety, a metal center, or the like, the composition of which is well understood by those skilled in the art. By way of illustration and not in limitation, suitable R groups include H, alkyl, alkenyl, or aryl. This reaction mechanism is based on the well known $S_NAr$ mechanism; for example, see *Nucleophilic Aromatic Displacement: The Influence of the Nitro Group*, Francois Terrier, VCH Publishing, Inc., New York, N.Y. pages 1–11 (1991). Preferably, these $S_NAr$ reactions are carried out in electron-deficient aromatic rings comprising at least one electron-withdrawing group.

In the second preferred reaction mechanism, an aryl reactant is substituted by a suitable amino group, which allows direct derivatization (e.g., after diazotization of the amino group) of the ring atom of the aryl group that is bound to the displaced amino group. There is no requirement for the atom of the aryl ring linked to the $O^2$-oxygen to be activated after it has been incorporated into the present inventive compound. However, if this atom is activated after being incorporated into the present inventive compound, then the diazeniumdiolate moiety to which it is bound may be displaced through further nucleophilic displacement (e.g., in a suitably strong base). Alternatively, an oxidative or electrophilic activation event can alter the present inventive compound so that the aryl ring atom linked to the $O^2$-oxygen becomes activated, thereby rendering the compound subject to further nucleophilic displacement, as observed above.

Advantageously, the compounds of the present invention have new and useful properties, which are not possessed by other nitric oxide/nucleophile adducts previously known in the art. In general, the compounds of the present invention are stable at neutral or acidic pH (i.e., at neutral or acidic pH, the compounds indicated by Formula I do not generate NO). Another advantageous property of the compounds of the present invention is that the $O^2$-aryl linkage is often susceptible to cleavage by nucleophiles, including hydroxide ions. When the typical $O^2$-aryl diazeniumdiolate or the oxidatively or electrophilically activated $O^2$-aryl diazeniumdiolate of the present invention is placed into a basic or nucleophilic environment, the aryl linkage to the $O^2$-oxygen can be broken. The resulting diazeniumdiolate ion spontaneously degrades via a predictable, first order mechanism, giving rise to NO. The resulting aryl group is substituted with a nucleophile provided by the environment. If the nucleophile provided by the environment is part of an enzyme, that enzyme can be inactivated. The susceptibility to nucleophilic attack of the $O^2$-aryl diazeniumdiolates also makes them particularly amenable to designing prodrugs for targeting nitric oxide to nucleophilic tissue components, body sites and microenvironments in the body.

The compounds of the present invention are also useful to identify and quantify individual thiols (organic —SH containing compounds) when the thiols are present in mixtures.

For example, a sample suspected to consist of $C_4$–$C_8$ straight-chain thiols can be analyzed by dissolving the product of Example 1 in tetrahydrofuran or another inert solvent, then mixing a molar excess of the resulting solution with the sample to be assayed. After the ensuing reaction is complete, an aliquot is subjected to HPLC analysis using an ultraviolet detection system. Peaks found in the resulting chromatogram can be identified by comparing their retention times to those of independently derivatized authentic standards of the individual $C_4$–$C_8$ straight-chain thiols, and quantified by transforming peak areas to concentrations via the individual standard curves.

With respect to the $O^2$-aryl diazeniumdiolates, "aryl group" as used herein refers to any aromatic group, regardless of whether it is part of a (homo)cyclic, heterocyclic, or polycyclic structure. The standard understanding of "aromatic" is used herein (See, e.g., L. G. Wade, Jr., *Organic Chemistry*, 2d Edition, Prentice Hall, Englewood Cliffs, N.J., 682–683 (1991)). The aryl group, as used herein, can also have a wide variety of substituent groups. Any suitable aryl substituent can be used providing that the substituent does not destroy the aromaticity of the aryl ring.

Turning to the aryl group Q of Formula I, Q is intended to include all aryl groups that are (or can be made) amenable to reaction with the $O^2$-oxygen atom of a diazeniumdiolate. The moiety Q thus includes homocyclic, heterocyclic, and polycyclic aromatic structures as well as derivatives thereof. Illustrative of the aryl groups Q are acridine, anthracene, benzene, benzofuran, benzothiophene, benzoxazole, benzopyrazole, benzothiazole, carbazole, chlorophyll, cinnoline, furan, imidazole, indole, isobenzofuran, isoindole, isoxazole, isothiazole, isoquinoline, naphthalene, oxazole, phenanthrene, phenanthridine, phenothiazine, phenoxazine, phthalimide, phthalazine, phthalocyanine, porphin, pteridine, purine, pyrazine, pyrazole, pyridazine, pyridine, pyrimidine, pyrrocoline, pyrrole, quinolizinium ion, quinoline, quinoxaline, quinazoline, sydnone, tetrazole, thiazole, thiophene, thyroxine, triazine, and triazole.

In keeping with the invention, each of these aromatic compounds Q can be variably derivatized with the numerous substituents well known in the art that are capable of being substituted into an aromatic ring so long as the aromaticity of the ring is maintained. For example, the substituents of the aryl moiety, Q, can include $X[N(O)NO]^-$, wherein X is as defined hereinafter and is the same as X of Formula I, halo, hydroxy, alkylthio, arylthio, alkoxy, aryloxy, amino, mono- or di-substituted amino, ammonio or substituted ammonio, nitroso, cyano, sulfonato, mercapto, nitro, oxo, $C_1$–$C_{24}$ aliphatic, $C_3$–$C_{12}$ oleinic, $C_3$–$C_{24}$, cycloalkyl, $C_3$–$C_{24}$ heterocycloalkyl, benzyl, phenyl, substituted benzyl, substituted phenyl, benzylcarbonyl, phenylcarbonyl, saccharides, substituted benzylcarbonyl, substituted phenylcarbonyl and phosphorus derivatives. Illustrative phosphorus derivatives include phosphate and phosphono moieties. Illustrative phosphate moieties include $(OH)_2P(O)O$— and substituted $(OH)_2P(O)O$-moieties, wherein one or more oxygen atoms can be independently replaced by S or NR', wherein R' is understood to be a $C_1$–$C_{10}$ containing aliphatic, cycloalkyl, or aryl group. Illustrative $C_1$–$C_{24}$ aliphatic substituents comprise $C_1$–$C_{24}$ acyl, and

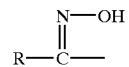

wherein R is hydrogen, substituted or unsubstituted $C_1$–$C_{23}$ aliphatic, substituted or unsubstituted $C_3$–$C_{23}$ cycloalkyl, substituted or unsubstituted $C_3$–$C_{12}$ olefinic, benzyl, phenyl, substituted benzyl or substituted phenyl, and said substituted benzyl or substituted phenyl is substituted with one to five substituents selected from the group consisting of nitro, halo, hydroxy, $C_1$–$C_{24}$ alkyl, $C_1$–$C_{24}$ alkoxy, amino, mono-$C_1$–$C_{24}$ alkylamino, di-$C_1$–$C_{24}$ alkylamino, cyano, phenyl and phenoxy. Preferred saccharides include ribose, glucose, deoxyribose, dextran, starch, glycogen, lactose, fucose, galactose, fructose, glucosamine, galactosamine, heparin, mannose, maltose, sucrose, sialic acid, and cellulose. Other preferred saccharides are phosphorylated, 3,5-cyclophosphorylated, and polyphosphorylated hexoses and pentoses.

Examples of substituted aryl compounds of the present invention that can be linked to the diazeniumdiolate group comprise dinitrophenol (a benzene), hypoxanthine (a purine), uridine (a pyrimidine), vitamin $K_5$ (a naphthalene) and ribosyl uridine (a nucleoside).

In another particular embodiment of the present invention, the aryl moiety is identical to or structurally analogous to molecules, or substituents thereof, normally found in living organisms. These biologically relevant groups can be selected from nucleotides, nucleosides, and nucleic acids, peptides, including peptide hormones, non-peptide hormones, vitamins and other enzyme cofactors such as porphyrins, and others. Examples of biologically relevant aryl groups are thyroxine, NAD (or NADH), chlorophyll, hypoxanthine, uridine, and vitamin $K_5$.

The following reaction schematics illustrate methods of preparing the $O^2$-aryl diazeniumdiolates of the present invention. In these illustrative reactions, in general, a solution of a diazeniumdiolate (X—$[N_2O_2^-]$) in 5% aqueous sodium bicarbonate. (which is weakly basic) is cooled to 0° C., preferably under a blanket of inert gas such as nitrogen. A solution containing one equivalent of the activated aromatic reagent in a solvent, such as t-butyl alcohol, dimethyl sulfoxide, or N,N-dimethylformamide, is then added slowly. While not being bound to any particular theory, it is believed that polar non-protic solvents are preferred. The reaction temperature is raised slightly for less reactive aryl moieties, for example, to ambient temperatures or higher. Generally, a precipitate forms upon addition. The mixture is then allowed to warm to room temperature gradually and stirred overnight. The product may be extracted with a suitable extraction agent, such as dichloromethane, and washed subsequently with cold dilute hydrochloric acid and then with sodium bicarbonate solution. The organic layer is dried over a suitable drying agent, such as sodium sulfate, filtered, preferably through a layer of anhydrous magnesium sulfate, and evaporated under vacuum to give the crude product. Usually, the product is solid. Recrystallization from ethanol or other suitable solvents is a preferred method of purifying the product. It will be appreciated by one skilled in the art that these conditions can be modified to suit the particular application of the artisan. Accordingly, alternative methods of preparation are also embraced.

Chlorinated quinoline and isoquinoline can be reacted with a diazeniumdiolate such that the Cl substituent is replaced by the O²-oxygen of a diazeniumdiolate, as shown below:

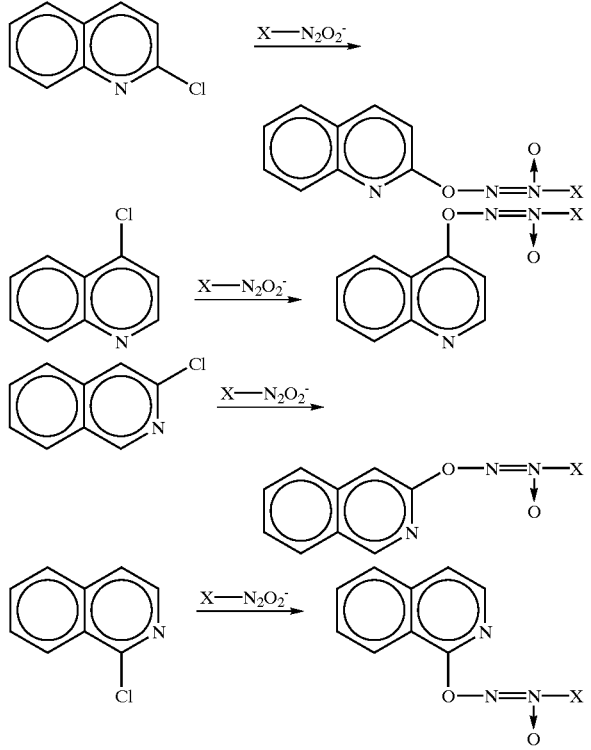

Additionally, quinazoline can be incorporated as shown:

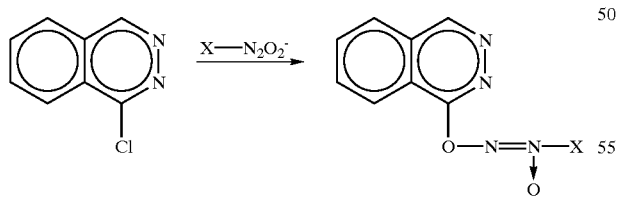

The phthalazines also are incorporated in accordance with the present invention, as indicated:

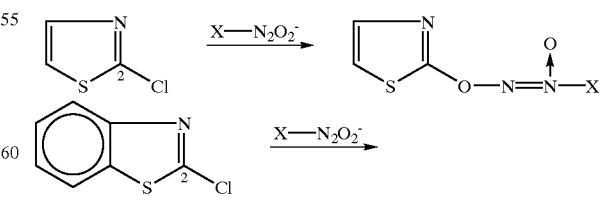

Acridine can be incorporated as indicated:

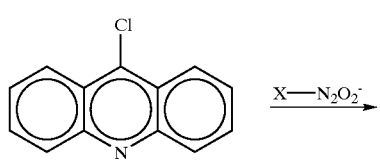

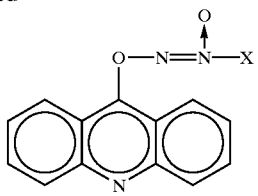

Cinnoline can also be incorporated as indicated:

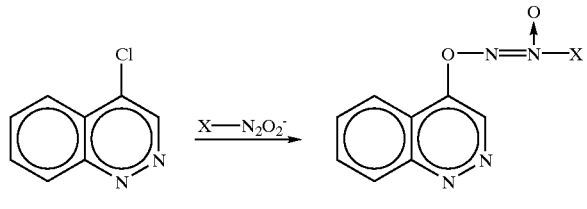

Quinoxaline can also be incorporated as indicated:

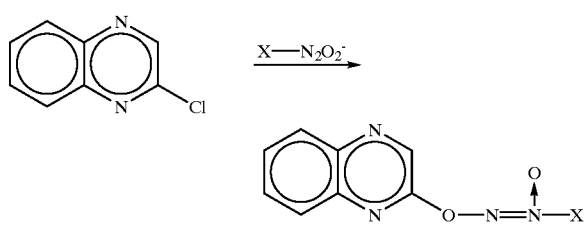

Oxygen- and sulfur-containing heteroaromatics can also be used as the aromatic reagent for O²-oxygen substitution of the diazeniumdiolate in accordance with the present invention. For example, oxazole and benzoxazole can be derivatized at the 2-position as indicated:

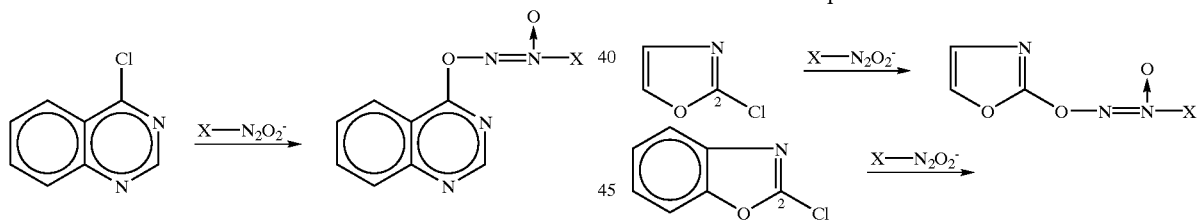

Similarly, thiazole and benzothiazole can also be derivatized at the 2-position.

A derivatized Vitamin $K_7$ can also be prepared, as indicated:

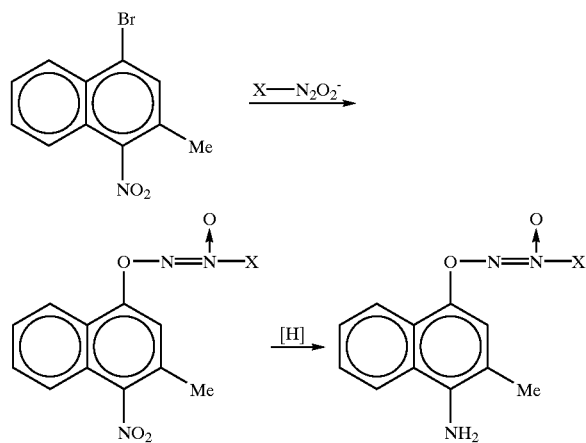

The $O^2$-diazeniumdiolated atom of the aryl ring in the right-most (directly above) structure is not activated. Therefore, the right-most structure is resistant to nucleophilic attack, which would re-generate $X$—$N_2O_2^-$, which, in turn, would spontaneously degrade to produce NO. Therefore, the right-most structure must undergo oxidative preactivation prior to nucleophilic attack in order to generate NO. This oxidative preactivation requirement would also be of advantage in targeting a cell or organ type that is uniquely able to perform the required oxidation, thereby limiting NO exposure to the desired tissue while avoiding exposure at other NO— sensitive portions of the anatomy.

Illustrative of the class of compounds requiring electrophilic preactivation is the compound indicated below:

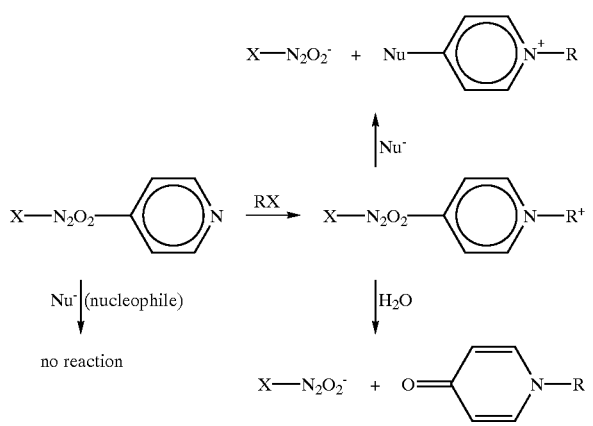

Triazines can likewise be the aromatic reagent that forms the $O^2$-aryl substituted diazeniumdiolates of the present invention as shown below. The synthesis of such compounds should enhance the potency of existing triazine-derived herbicides.

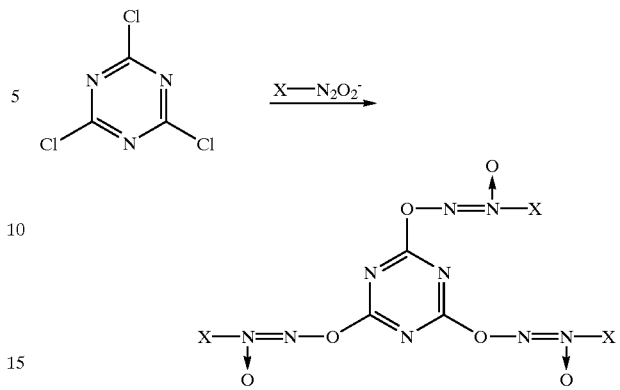

Nucleic acids and the nitrogenous bases they comprise (including ribosylated bases) can also be used as the aromatic reagent to form the $O^2$-aryl substituted diazeniumdiolates of the present invention. This is illustrated in Example 13.

Another interesting $O^2$-arylated diazeniumdiolate is the one shown as the product in the reaction below; it can co-generate NO and allopurinol on hydrolysis.

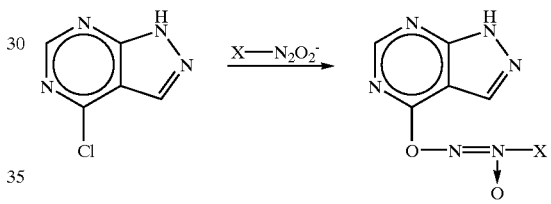

Advantageously, allopurinol is already known to be pharmaceutically useful. Thus, by converting known pharmaceutically useful compounds containing a suitable aryl group to the $O^2$-aryl diazeniumdiolates of the present invention, the present invention allows existing drugs to be enhanced by the release of NO.

Similarly, a derivative of a biopterin diazeniumdiolate can be prepared from a substituted pteridine, as indicated below.

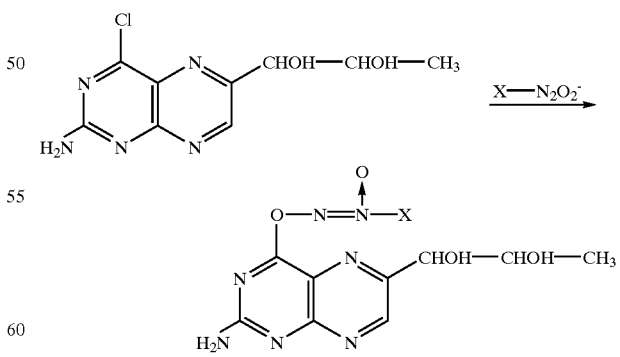

An example of a suitable aryl substitution that utilizes linkage through a heteroatom is shown in the following scheme which can be effected by reaction with BuONO or other suitable nitrosating agents.

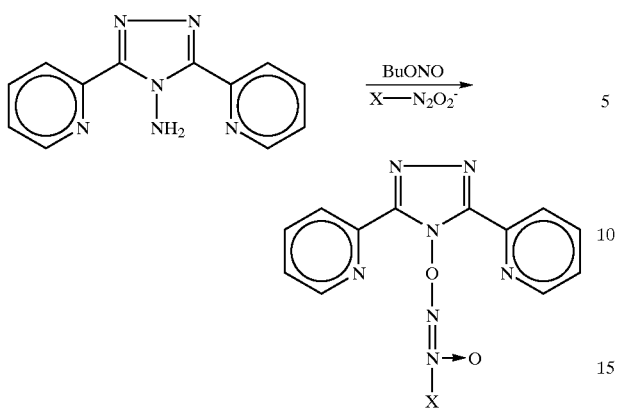

A structural analog of Bendazac, a well-known anti-inflammatory agent, can be prepared as indicated:

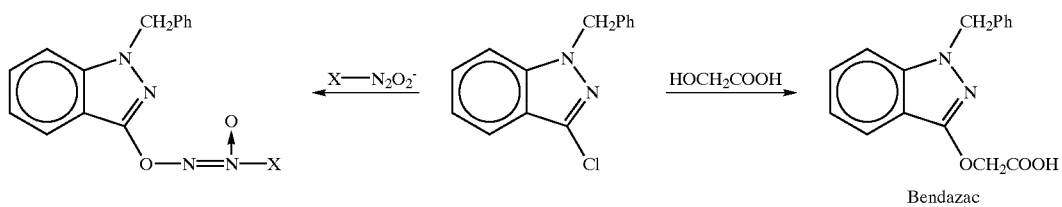

Bendazac

In accordance with the invention, any of the compounds in the class of compounds defined as diazeniumdiolates can be subjected to $O^2$-aryl substitution. Thus, for the compounds having Formula I, X can be any organic or inorganic moiety. Preferably, X contains atoms other than carbon and hydrogen, and is linked to the nitrogen of the $N_2O_2^-$ group through an atom other than carbon. Most preferably, X is an amine, and is linked to the nitrogen of the $N_2O_2^-$ group through a nitrogen atom. Suitable moieties of X also include, but are not limited to, $C_1$–$C_{24}$ aliphatic, aryl, and nonaromatic cyclic. By "aliphatic" is meant acyclic moieties containing carbon and hydrogen and optionally containing nitrogen, oxygen, sulfur, phosphorus, and halogens. By "aryl" is meant, as hereinabove, a moiety containing at least one aromatic ring. Preferably, the aryl moiety is a $C_3$–$C_{30}$-containing moiety. By non-aromatic cyclic is meant a moiety containing at least one ring structure and no aromatic rings. Preferably, the non-aromatic cyclic moiety is a $C_3$–$C_{30}$-containing moiety.

The moiety X of Formula I can be unsubstituted or substituted with suitable additional moieties, such as, for example, —[N(NO)O—], halo, hydroxy, alkylthio, alkoxy, aryloxy, amino, mono- or di-substituted amino, cyano, sulfonato, mercapto, nitro, substituted or unsubstituted $C_1$–$C_{12}$ aliphatic, substituted or unsubstituted $C_3$–$C_8$ cycloalkyl, substituted or unsubstituted $C_3$–$C_8$ heterocycloalkyl, substituted or unsubstituted $C_3$–$C_{12}$ olefinic, benzyl, phenyl, substituted benzyl, substituted phenyl, benzylcarbonyl, phenylcarbonyl, saccharides, substituted benzylcarbonyl, substituted phenylcarbonyl and phosphorus derivatives. Illustrative phosphorus derivatives include phosphato and phosphono moieties. Illustrative phosphato moieties include $(OH)_2P(O)O$— and substituted $(OH)_2P(O)O$— moieties, wherein one or more oxygen atoms can be independently replaced by S or NR', wherein R' is understood to be a $C_1$–$C_8$-containing aliphatic, cycloalkyl, or aryl group. Preferred $C_1$–$C_{12}$ aliphatic substituents comprise $C_1$–$C_{12}$ acyl, and (III)

$$\underset{R-C}{\overset{N-OH,}{\|}}$$

wherein R is $C_1$–$C_{10}$ substituted or unsubstituted aliphatic, $C_3$–$C_{11}$ olefinic, $C_3$–$C_8$ substituted or unsubstituted cycloalkyl, benzyl, phenyl, substituted benzyl or substituted phenyl, and said substituted benzyl or substituted phenyl is substituted with one or two substituents selected from the group consisting of halogen, hydroxy, $C_1$–$C_4$ alkyl, $C_1$–$C_4$ alkoxy, amino, mono-$C_1$–$C_4$ alkylamino, di-$C_1$–$C_4$ alkylamino, phenyl and phenoxy. Preferred saccharides and polysaccharides include ribose, glucose, deoxyribose, dextran, starch, glycogen, lactose, galactose, fructose, glucosamine, galactosamine, heparin, mannose, maltose, sucrose, sialic acid, and cellulose. Other preferred saccharides are phosphorylated, 3,5-cyclophosphorylated, and polyphosphorylated pentoses and hexoses.

In one embodiment of the invention, X is an inorganic moiety as described in U.S. Pat. No. 5,212,204. Preferred embodiments of Formula I, in which X is inorganic, are $^-O_3S$— (sulfite) and —$O^-$ (oxide).

In another embodiment of the present invention, X is a polyamine as defined in U.S. Pat. No. 5,155,137. Thus, the polyamine substituted $O^2$-aryl diazeniumdiolates have the formula

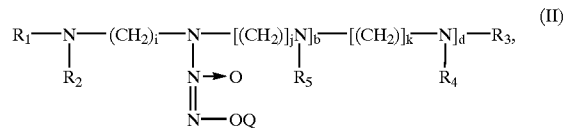

wherein Q is the same as the Q in Formula I and is defined as above, b and d can be the same or different and are zero or one, $R^1$, $R^2$, $R^3$, $P^4$, and $R^5$ are the same or different and comprise hydrogen, substituted or unsubstituted $C_3$–$C_8$ cycloalkyl, substituted or unsubstituted $C_1$–$C_{12}$ straight or branched chain alkyl, substituted or unsubstituted benzyl, substituted or unsubstituted benzoyl, substituted or unsubstituted $C_3$–$C_{12}$ olefinic, phthaloyl, acetyl, trifluoroacetyl, p-toluyl, t-butoxycarbonyl, or 2,2,2-tri-halo-t-butoxycarbonyl. The values of i, j, and k in Formula II can be the same or different and are integers from 2 to 12.

In a preferred embodiment of the present invention the $O^2$-aryl diazeniumdiolates are derived from the compounds disclosed in U.S. Pat. Nos. 5,039,705 (Keefer et al.) and 4,954,526 (Keefer et al.) and, thus, have the formula

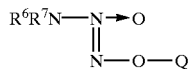

wherein $R^6$ and $R^7$ can be the same or different and are chosen from H, $C_1$–$C_{12}$ straight chain alkyl, $C_1$–$C_{12}$ alkoxy or acyloxy substituted straight chain alkyl, $C_2$–$C_{12}$ hydroxy or halo substituted straight chain alkyl, $C_3$–$C_{12}$ branched chain alkyl, $C_3$–$C_{12}$ hydroxy, halo, alkoxy, or acyloxy substituted branched chain alkyl, $C_2$–$C_{12}$ straight chain olefinic and $C_3$–$C_{12}$ branched chain olefinic, which are unsubstituted or which are substituted with hydroxy, alkoxy, acyloxy, halo or benzyl, provided that both $R^6$ and $R^7$ are not H; or $R^6$ and $R^7$, together with the nitrogen atom to which they are bonded, form a heterocyclic ring selected from the group consisting of:

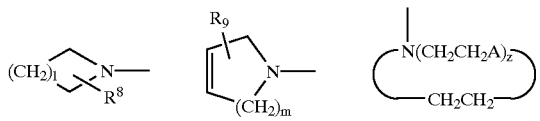

wherein A is N, O, or S, w is 1 to 12, y is 1 or 2, z is 1 to 5, $R^8$ is hydrogen, $C_1$–$C_8$ straight chain alkyl, $C_3$–$C_8$ branched chain alkyl, $C_3$–$C_8$ cycloalkyl, unsubstituted or substituted aryl, such as phenyl, tolyl or the like, and $R^9$ is hydrogen, $C_1$–$C_6$ straight chain alkyl or $C_3$–$C_6$ branched chain alkyl. Exemplary aza crown groups are 1-aza-12-crown-4, 1-aza-15-crown-5, and 1-aza-18-crown-6. Where A is nitrogen, the nitrogen atom, itself, can be substituted, as described, for example, in U.S. application Ser. No. 08/475,732, which is incorporated by reference herein.

Further examples include the $O^2$-aryl substituted diazeniumdiolates derived from the compounds disclosed in U.S. Pat. No. 5,250,550, previously incorporated in its entirety by reference, and, thus, have the formula

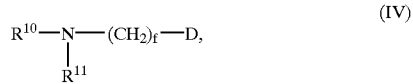

wherein D is

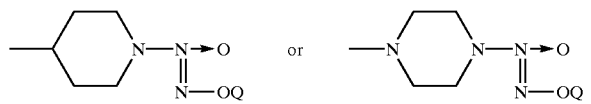

and wherein $R^{10}$ and $R^{11}$ are the same or different. The substituents $R^{10}$ and $R^{11}$ can be any suitable group, examples of which include hydrogen, $C_3$–$C_8$ cycloalkyl, $C_1$–$C_2$ straight or branched chain alkyl, benzyl, benzoyl, phthaloyl, acetyl, trifluoroacetyl, p-toluyl, t-butoxycarbonyl, and 2,2,2-trihalo-t-butoxycarbonyl. In Formula IV, f is an integer from 0 to 12.

Preferred $O^2$-aryl substituted diazeniumdiolates also include those of Example 14.

An alternative method of preparing $O^2$-arylated diazeniumdiolates is possible through adaptation of the following literature reaction (Stevens, *J.Org. Chem.* 29: 311–315 (1964)).

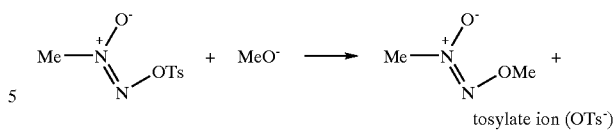

tosylate ion (OTs⁻)

By substituting aryloxy anion ArO⁻ for the methoxide of Stevens's reaction, it is possible to obtain $O^2$-aryl diazeniumdiolates of varied structure. Similarly, it is possible to obtain derivatives corresponding to ArS⁻ species.

$O^2$-glycosylated diazeniumdiolates and 1-[(2-carboxylato) pyrrolidin-1-yl] diazeniumdiolates The present invention also provides two other new classes of diazeniumdiolates, one class of which contains a hydrolytically labile group (R), which, upon cleavage to the free diazeniumdiolate (NO donor) X—NO=NO⁻, releases an innocuous and possibly beneficial saccharide and allows advantage to be taken of saccharide-based receptor-mediated phenomena. The other class of diazeniumdiolates provides, among others, prodrugs of the salt disodium 1-[(2-carboxylato)pyrrolidin-1-yl]diazen-1-ium-1,2-diolate (PROLI/NO), which is an ultrafast NO donor of proven effectiveness as an antithrombotic agent and a vasodilator but is inherently extremely difficult to derivatize, due to its instability (Saavedra et al., *J. Med. Chem.* 31:4361–4365 (1996); and U.S. Pat. No. 5,632,981 (Saavedra et al.)). The newly discovered ability to generate prodrugs of the ultrafast NO donor PROLI/NO allows the PROLI/NO prodrugs to move freely through the circulatory system until they reach the desired organ or cell type for metabolic removal of the stabilizing $O^2$-protecting group, thereby providing a rapid release of NO at the specific or preferred site and obviating the need for administration by infusion at a controlled rate in the vicinity of the target tissue. Additionally, the corresponding nitrosamine, N-nitrosoproline, if formed in the biological medium, does not pose a carcinogenic threat, unlike other nitrosamines.

Accordingly, the present invention provides $O^2$-glycosylated 1-substituted diazen-1-ium-1,2-diolates ($O_2$-glycosylated diazeniumdiolates) and $O^2$-substituted 1-[(2-carboxylato)pyrrolidin-1-yl]diazen-1-ium-1,2-diolates (1-[(2-carboxylato)pyrrolidin-1-yl] diazeniumdiolates), both of which can be represented by the formula:

(Ia)

In Formula Ia, X and R are organic and/or inorganic moieties as defined herein.

$O^2$-glycosylated diazeniumdiolates

With respect to the $O^2$-glycosylated diazeniumdiolates, any of the compounds in the class of compounds defined as diazeniumdiolates (see e.g., U.S. Pat. Nos. 5,039,705, 5,208, 233, 5,155,137, 5,250,550, 5,389,675, 5,525,357, 5,405,919 and related patents and patent applications) can be subjected to $O^2$-glycosylation, provided that the $O^2$ of the diazeniumdiolate is available for glycosylation. The moiety R of Formula Ia can be any saccharide, which is attached to the $O^2$ of the diazeniumdiolate by the 2 position of a pyranose or furanose ring. The saccharide can be functionalized. Desirably, the saccharide and its derivatives are hydrolyzable at physiological pH. The saccharide can be a monosaccharide, disaccharide, such as sucrose or maltose, an oligosaccharide or a polysaccharide. Preferred saccharides and polysaccharides include, among others, ribose, glucose, deoxyribose, fucose, lactose, galactose, fructose, glucosamine, galactosamine, mannose, maltose, sucrose, and the many saccharide and oligosaccharide units that serve as recognition sequences in receptor-mediated cellular interactions. Other preferred saccharides include those that are phosphorylated, 3,5-cyclophosphorylated, and polyphosphorylated pentoses and hexoses.

By way of illustration, the saccharide residue (shown attached to the diazeniumdiolate for illustrative purposes) can be an amino sugar, such as a glucosamine or a substituted glucosamine having the structure:

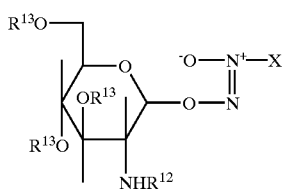

wherein $R^{12}$ and $R^{13}$ can be the same or different and are a hydrogen, a $C_{1-6}$ alkyl, an acyl, a phosphate, a sulfate, a peptide or a protein. The saccharide residue can be, for example, glucuronic acid or a derivative thereof:

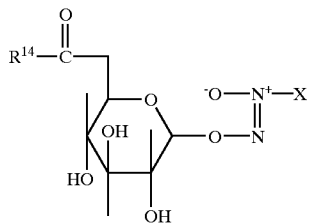

wherein $R^{14}$ is $X^1R^{15}R^{16}$, wherein $X^1$ is N, O or S and, when $X^1$ is N, $R^{15}$ and $R^{16}$ are independently a hydrogen or a substituted or an unsubstituted $C_{1-24}$ alkyl, $C_{3-24}$ cycloalkyl, $C_{2-24}$ olefinic, aryl. (such as acridine, anthracene, benzene, benzofuran, benzothiophene, benzoxazole, benzopyrazole, benzothiazole, carbazole, chlorophyll, cinnoline, furan, imidazole, indole, isobenzofuran, isoindole, isoxazole, isothiazole, isoquinoline, naphthalene, oxazole, phenanthrene, phenanthridine, phenothiazine, phenoxazine, phthalimide, phthalazine, phthalocyanine, porphin, pteridine, purine, pyrazine, pyrazole, pyridazine, pyridine, pyrimidine, pyrrocoline, pyrrole, quinolizinium ion, quinoline, quinoxaline, quinazoline, sydnone, tetrazole, thiazole, thiophene, thyroxine, triazine, and triazole), or heterocyclic group, such as glycosyl and the like, and when $X^1$ is O or S, there is no $R^{16}$ group.

Alternatively, when X1 is nitrogen, $R^{15}$ and $R^{16}$ form a heterocyclic ring selected from the group consisting of:

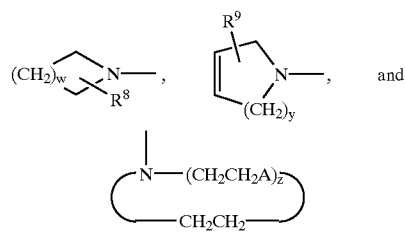

wherein A is N, O, or S, w is 1–12, y is 1 or 2, z is 1–5, $R^8$ is hydrogen, a $C_{1-8}$ straight chain alkyl, a $C_{3-8}$ branched chain alkyl, a $C_{3-8}$ cycloalkyl, an aryl (such as phenyl, tolyl or the like), or carboxylato and derivatives thereof as further described herein, and $R^9$ is hydrogen, a $C_{1-6}$ straight chain alkyl or a $C_{3-6}$ branched chain alkyl.

The aforementioned groups can be unsubstituted or substituted as appropriate.

Exemplary aza crown groups (i.e., where A is N) are 1-aza-12-crown-4, 1-aza-15-crown-5, and 1-aza-18-crown-6. Where A is nitrogen, the nitrogen atom, itself, can be substituted, as described, for example, in U.S. patent application Ser. No. 08/475,732.

Further with respect to the $O^2$-glycosylated diazeniumdiolates, the moiety attached to the carbonyl group through $X^1$ can be anything that does not interfere with the cleavage to the diazeniumdiolate anion.

Further with respect to the $O^2$-glycosylated diazeniumdiolates, the moiety attached to the carbonyl group through $X^1$ can be anything that does not interfere with the cleavage to the diazeniumdiolate anion.

Preferably, the moiety X contains atoms other than carbon and hydrogen, and is linked to the nitrogen of the $N_2O_2^-$ group through an atom other than carbon. Most preferably, X is an amino group, and is linked to the nitrogen of the $N_2O_2^-$ group through a nitrogen atom. Suitable moieties of X include, but are not limited to, $C_{1-24}$ aliphatic, aryl and non-aromatic cyclic groups. By "aliphatic" is meant an acyclic moiety containing carbon and hydrogen and optionally containing nitrogen, oxygen, sulfur, phosphorus or a halogen. By "aryl" is meant a moiety containing at least one aromatic ring. Preferably, the aryl moiety is a $C_{6-30}$ moiety. By "non-aromatic cyclic" is meant a moiety containing at least one ring structure and no aromatic rings. Preferably, the non-aromatic cyclic moiety is a $C_{6-30}$ moiety. Further, X can be unsubstituted or substituted with suitable additional moieties, such as, for example, —[N(NO)O$^-$], a halo, a hydroxy, an alkylthio, an alkoxy, an aryloxy, an amino, a mono- or di-substituted amino, a cyano, a sulfonato, a mercapto, a nitro, a substituted or unsubstituted $C_{1-12}$ aliphatic, a substituted or unsubstituted $C_{3-8}$ cycloalkyl, a substituted or unsubstituted $C_3$–$C_{12}$ olefinic, a substituted or unsubstituted $C_{3-8}$ heterocycloalkyl, a benzyl, a phenyl, a substituted benzyl, a substituted phenyl, a benzylcarbonyl, a phenylcarbonyl, a saccharide, a substituted benzylcarbonyl, a substituted phenylcarbonyl and a phosphorus derivative. Illustrative phosphorus derivatives include phosphato and phosphono moieties. Illustrative phosphato moieties include $(OH)_2P(O)O—$ and substituted $(OH)_2P(O)O—$ moieties, wherein one or more oxygen atoms can be independently replaced by S or $NR^{17}$, wherein $R^{17}$ is understood to be a $C_{1-8}$ aliphatic, a

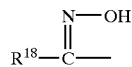

wherein $R^{18}$ is a $C_{1-10}$ unsubstituted or substituted aliphatic, a $C_{3-8}$ unsubstituted or substituted cycloalkyl, benzyl, phenyl, substituted benzyl or substituted phenyl. When the benzyl or phenyl is substituted, preferably it is substituted with one or two substituents selected from the group consisting of halogen, hydroxy, a $C_{1-4}$ alkyl, a $C_{1-4}$ alkoxy, an amino, a mono-$C_{1-4}$ alkylamino, a di-$C_{1-4}$ alkylamino, phenyl and phenoxy.

In one embodiment of the invention, X in Formula Ia is an inorganic moiety as described in U.S. Pat. No. 5,212,204. Preferred embodiments of Formula Ia, in which X is inorganic, are $^-O_3S-$ (sulfite) and $-O^-$ (oxide).

In another embodiment of the present invention, X in Formula Ia is a polyamine as defined in U.S. Pat. No. 5,250,550. Thus, the polyamine $O^2$-glycosylated diazeniumdiolates have the formula

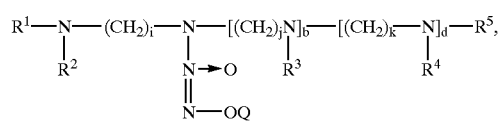 (II)

wherein Q is the same as the R in Formula Ia and is defined as above, b and d can be the same or different and are zero or one, $R^1$, $R^2$, $R^3$, $R^4$, and $R^5$ are the same or different and are hydrogen, substituted or unsubstituted $C_{3-8}$ cycloalkyl, substituted or unsubstituted $C_{1-12}$ straight or branched chain alkyl, substituted or unsubstituted benzyl, substituted or unsubstituted benzoyl, substituted or unsubstituted $C_3$–$C_{12}$ olefinic, phthaloyl, acetyl, trifluoroacetyl, p-toluyl, t-butoxycarbonyl, or 2,2,2-tri-halo-t-butoxycarbonyl. The values of i, j, and k in Formula II can be the same or different and are integers from 2 to 12.

In a preferred embodiment of the present invention, the diazeniumdiolates are derived from the compounds disclosed in U.S. Pat. Nos. 5,039,705 (Keefer et al.) and 4,954,526 (Keefer et al.), and, thus, have the formula

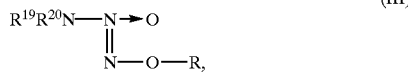 (III)

wherein R is the same as the R in Formula Ia and is defined as above, $R^{19}$ and $R^{20}$ are the same or different and are hydrogen, a $C_{1-12}$ straight chain alkyl, a $C_{3-12}$ branched chain alkyl, or a $C_{2-12}$ straight or $C_{3-12}$ branched chain olefinic, provided that both $R^{19}$ and $R^{20}$ are not hydrogen. Any of the aforementioned substituents can be unsubstituted or substituted with an alkoxy, an acyloxy, an acylthio, a hydroxy, a halo or a benzyl group.

Alternatively, $R^{19}$ and $R^{20}$, together with the nitrogen atom to which they are bonded, form a heterocyclic ring selected from the group consisting of:

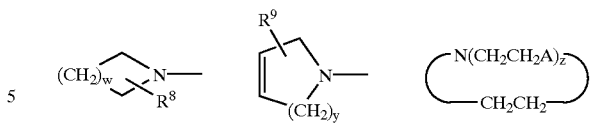

wherein A is N, O, or S, w is 1–12, y is 1 or 2, z is 1–5, R is hydrogen, a $C_{1-8}$ straight chain alkyl, a $C_{3-8}$ branched chain alkyl, a $C_{3-8}$ cycloalkyl, a substituted or an unsubstituted aryl (such as phenyl, tolyl or the like), or carboxylato and derivatives thereof as further described herein, and $R^9$ is hydrogen, a $C_{1-6}$ straight chain alkyl or a $C_{3-6}$ branched chain alkyl. The aforementioned groups can be unsubstituted or substituted as appropriate.

Exemplary aza crown groups (i.e., where A is N) are 1-aza-12-crown-4, 1-aza-15-crown-5, and 1-aza-18-crown-6. Where A is nitrogen, the nitrogen atom, itself, can be substituted, as described, for example, in U.S. patent application Ser. No. 08/475,732.

Further examples include the $O^2$-glycosylated diazeniumdiolates derived from the compounds disclosed in U.S. Pat. No. 5,250,550, and, thus, have the formula

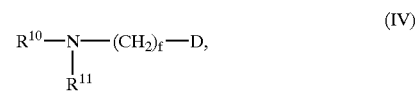 (IV)

wherein D is

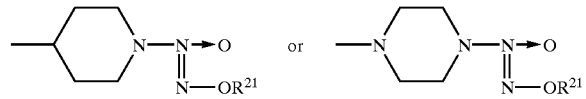

and wherein $R^{21}$ is the same as the R in the saccharide of Formula Ia and is defined as above, and $R^{10}$ and $R^{11}$, which can be the same or different, can be any suitable group, examples of which include hydrogen, a $C_{3-8}$ cycloalkyl, a $C_{1-12}$ straight or branched chain alkyl, benzyl, benzoyl, phthaloyl, acetyl, trifluoroacetyl, p-toluyl, t-butoxycarbonyl and 2,2,2-trihalo-t-butoxycarbonyl. In Formula IV, f is an integer from 0 to 12.

A preferred $O^2$-glycosylated diazeniumdiolate is one in which, with respect to Formula Ia, X is $N(CH_2CH_2NH_2)_2$ and R is fucose or mannose.

The above compounds can be prepared in accordance with methods known to those of skill in the art. Reagents for glycopyranosylation include acetobromo-α-galactose and acetobromoglucosamine. Reagents for glycofuranosylation include tribenzyl-α-arabinofuranosyl bromide and bromoacetylxylose.

Oligosaccharides are commercially available from, for example, Sigma Chemical Co. (St. Louis, Mo.) and Carbomer Specialty Biochemicals and Polymers (Westborough, Mass.). In addition, oligosaccharides can be synthesized in accordance with well-established procedures, including chemical and enzymatic preparation, such as those described in *Preparative Carbohydrate Chemistry*, Stephen Hanessian, ed., Marcel Dekker, New York, N.Y. (1997) and *Polysaccharides in Medicinal Applications*, Severian Dumitriu, ed., Marcel Dekker, New York, N.Y. (1996).

A protected straight- or branched-chain polysaccharide can be activated toward reaction with the diazeniumdiolate ion by halogenation of the anomeric terminus, followed by glycosylation of the diazeniumdiolate. Activated disaccharides for generation of $O^2$-glycosylated diazeniumdiolates include acetobromo-α-maltose and acetobromo-α-lactose.

$O^2$-Glycosylated diazeniumdiolates are useful where molecular signalling and recognition processes, including cell adhesion, involve carbohydrates. For example, $O^2$-glycosylated diazeniumdiolates are believed to be useful in the treatment of infection, such as that due to a parasite (e.g., leishmania), a virus or a bacterium, as well as inflammation and metastasis. In this regard, an $O^2$-glycosylated diazeniumdiolate can be prepared so as to be directed to a mannose-fucose receptor as exemplified in Example 36. It is believed that the sugar residue, in this instance mannose, protects the diazeniumdiolate. The mannose binds to the mannose-fucose receptor on a macrophage, and the $O^2$-mannosylated diazeniumdiolate is imported into the cell, where the sugar residue is cleaved, and NO is released.

1-[(2-CARBOXYLATO)PYRROLIDIN-1-YL] DIAZENIUMDIOLATES

With respect to the 1-[(2-carboxylato)pyrrolidin-1-yl] diazeniumdiolates, the moiety X of Formula Ia can be

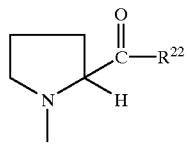

such that the 1-[(2-carboxylato)pyrrolidin-1-yl] diazeniumdiolates can be structurally represented by the formula:

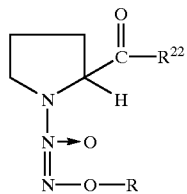

wherein $R^{22}$ is hydrogen, hydroxyl, OM, wherein M is a cation, halo, or $X^1R^{23}R^{24}$, wherein $X^1$ is N, O or S and, when $X^1$ is N, $R^{23}$ and $R^{24}$ are independently a substituted or an unsubstituted $C_{1-24}$ alkyl, $C_{3-24}$ cycloalkyl, $C_{2-24}$ olefinic, aryl (such as acridine, anthracene, benzene, benzofuran, benzothiophene, benzoxazole, benzopyrazole, benzothiazole, carbazole, chlorophyll, cinnoline, furan, imidazole, indole, isobenzofuran, isoindole, isoxazole, isothiazole, isoquinoline, naphthalene, oxazole, phenanthrene, phenanthridine, phenothiazine, phenoxazine, phthalimide, phthalazine, phthalocyanine, porphin, pteridine, purine, pyrazine, pyrazole, pyridazine, pyridine, pyrimidine, pyrrocoline, pyrrole, quinolizinium ion, quinoline, quinoxaline, quinazoline, sydnone, tetrazole, thiazole, thiophene, thyroxine, triazine, and triazole), or heterocyclic group, such as glycosyl, and the like, and when $X^1$ is O or S, there is no $R^{24}$ group. Alternatively, when $X^1$ is nitrogen, $R^{23}$ and $R^{24}$, together with the nitrogen to which they are bonded, form a heterocyclic ring, such as a heterocyclic ring selected from the group consisting of:

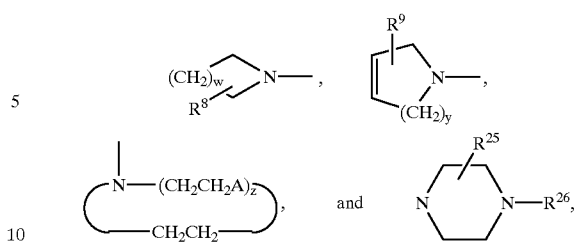

in which A is N, O or S, w is 1 to 12, y is 1 or 2, z is 1 to 5, $R^8$, $R^9$, $R^{25}$ and $R^{26}$ are hydrogen, a $C_{1-8}$ straight chain alkyl, a $C_{3-8}$ branched chain alkyl, a $C_{3-8}$ cycloalkyl, or an aryl. The aforementioned groups can be unsubstituted or substituted as appropriate.

The R substituent on the nitrogen (N–4) can be a hydrogen, a $C_{1-8}$ alkyl group, an aryl group, or $C(O)$-$YR^{27}$, wherein Y is sulfur or oxygen, or nitrogen and $R^{27}$ is $CH_2OCH_3$, vinyl, a $C_{1-9}$ straight chain alkyl, a $C_{3-6}$ branched chain alkyl, a $C_{3-8}$ cycloalkyl, polyethylene glycol, polysaccharide, or other polymer, a peptide, or a protein. $YR^{27}$ can be an activating linker, such as a hydroxy succinimidyl group, for linkage to proteins, peptides, phospholipids, polysaccharides, oligosaccharides, purines, pyrimidines, and biocompatible polymers (i.e., polyethylene glycol, polylactides, and polycaprolactone). $YR^{27}$ can be an activating moiety for the carbonyl group, making the carbonyl group an electrophilic site that reacts with nucleophilic functionalities of oligopeptides, polyamines and proteins. $YR^{27}$ can cause the carbonyl group to react with many nucleophiles, and can react with a polymer, such as polyethylene glycol, to form a polymer-bound compound.

Further with respect to the 1-[(2-carboxylato)pyrrolidin-1-yl]diazeniumdiolates, the moiety R of Formula Ia can be any covalently bound organic or inorganic moiety, which is other than hydrogen and is a $C_{1-12}$ straight chain or $C_{3-12}$ branched chain alkyl, a $C_{2-12}$ straight chain or $C_{3-12}$ branched chain olefinic, a $C_{1-12}$ acyl, sulfonyl, $C_{3-12}$ cycloalkyl, carboxamido, a glycosyl group as described above, an aryl group as described above, or a group of the formula —$(CH_2)_n$—ON=N(O)$NR^{28}R^{29}$, wherein n is an integer of 2–8, and $R^8$ and $R^9$ are independently a $C_{1-12}$ straight chain alkyl, a $C_{3-12}$ branched chain alkyl, a $C_{1-12}$ straight chain or $C_{3-12}$ branched chain olefinic, or $R^{28}$ and $R^{29}$, together with the nitrogen atom to which they are bonded, form a heterocyclic group, preferably a pyrrolidino, piperidino, piperazino or morpholino group. The aforementioned R groups can be unsubstituted or substituted as appropriate. Preferred substitutions include those made with hydroxy, halo, acyloxy, alkoxy, acylthio, or benzyl.

The above compounds can be prepared in accordance with methods known to those of skill in the art. For example, see Sanger, *Biochem. J.* 39: 507–515 (1945).

$O^2$-Substituted 1-[(2-carboxylato)pyrrolidin-1-yl] diazeniumdiolates offer advantages over other diazeniumdiolates in that they are more stable in aqueous solution than the $O^2$-unsubstituted anion and, in many cases, they can be activated for NO release by enzymatic action. Furthermore, if an N-nitroso derivative is formed by net formal cleavage of the N—N double bond of the 1-[(2-carboxylato)pyrrolin-1-yl]diazen-1-ium-1,2-diolate, the N-nitroso compound is noncarcinogenic. Such compounds are believed to be particularly useful in the treatment of fulminant liver failure, malaria, respiratory problems, impotence, and a variety of cardiovascular/hematologic disorders.

Polymer Bound Diazeniumdiolates

Another particularly useful embodiment of the present invention comprises $O^2$-aryl diazeniumdiolates of Formula I or $O^2$-glycosylated diazeniumdiolates of Formula Ia, wherein X is a polymer, or wherein any $O^2$-aryl diazeniumdiolate or $O^2$-glycosylated diazeniumdiolate of the present invention is incorporated into a polymeric matrix. PROLI/NO also can be polymer bound—through $R^{20}$ as well as R. Both of these embodiments result in the $N_2O_2^-$ functional group being "bound to the polymer." By "bound to a polymer," it is meant that the $N_2O_2^-$ functional group is associated with, part of, incorporated with or contained within the polymeric matrix physically or chemically.

Physical association or bonding of the $N_2O_2^-$ functional group to the polymer may be achieved by coprecipitation of the polymer with a nitric oxide/nucleophile complex as well as by covalent bonding of the $N_2O_2^-$ group to the polymer. Chemical bonding of the $N_2O_2^-$ group to the polymer may be by, for example, covalent bonding of the nucleophilic moiety of the nitric oxide/nucleophile adduct to the polymer such that the nucleophilic residue to which the $N_2O_2^-$ group is attached forms part of the polymer, itself, i.e., is in the polymer backbone or is attached to pendant groups on the polymer backbone. The manner in which the nitric oxide-releasing $N_2O_2^-$ functional group is associated with, part of, or incorporated with or contained within, i.e., "bound" to the polymer is inconsequential to the present invention and all means of association, incorporation and bonding are contemplated herein.

Site-specific application of the polymer-bound adduct composition enhances the selectivity of action of the nitric-oxide releasing $N_2O_2$ functional group. If $N_2O_2^-$ functional groups attached to the polymer are necessarily localized, then the effect of their nitric oxide release will be concentrated in the tissues with which they are in contact. If the polymer is soluble, selectivity of action can still be arranged, for example, by linkage to or derivatization of an antibody specific to the target tissue. Similarly, linkage of $N_2O_2^-$ groups to small peptides that mimic the recognition sequences of ligands for important receptors provides localized nitric oxide release, as would linkage to oligonucleotides capable of site-specific interactions with target sequences in a nucleic acid.

The $O^2$-diazeniumdiolates of the present invention can be derived from the materials disclosed in U.S. Pat. Nos. 5,525,357 (Keefer et al:) and 5,405,919 (Keefer et al.), and in U.S. patent application Ser. No. 08/419,424 (Smith et al.), each of which is incorporated by reference. Any of a wide variety of polymers can be used in the context of the present invention. It is only necessary that the polymer selected is biologically acceptable. Illustrative of polymers suitable for use in the present invention are polyolefins, such as polystyrene, polypropylene, polyethylene, polytetrafluorethylene, polyvinyl chloride, polyvinylidene difluoride, and polyethers such as polyethylene glycol, polysaccharides such as dextran, polyesters such as poly (lactide/glycolide), polyamides such as nylon, polyurethanes, polyethyleneimines, biopolymers such as peptides, proteins, oligonucleotides, antibodies and nucleic acids, starburst dendrimers, polysaccharides, and the like.

In this regard, a polymer containing a diazeniumdiolate can be reacted with a saccharide, such that the saccharide becomes bound to the $N_2O_2^-$ functional group.

Formation of a diazeniumdiolate from a biopolymer provides a biopolymer-bound diazeniumdiolate composition that can be applied with specificity to a biological site of interest. Site-specific application of the biopolymer-bound diazeniumdiolate enhances the selectivity of action of the nitric oxide-releasing diazeniumdiolate, which occurs following the cleavage of the $O^2$-aryl or $O^2$-glycosylated bond or the O—R bond in PROLI/NO (see pg. 33). As with the other polymers disclosed above, if the diazeniumdiolate attached to the biopolymer is localized because of the inherent properties of the molecule, then the effect of its nitric oxide release will be concentrated in the tissues with which they are in contact. If the biopolymer is soluble, selectivity of action can still be arranged, for example, by attachment to or derivatization of an antibody specific to the target tissue. Similarly, linkage of diazeniumdiolate groups to small peptides that mimic the recognition sequences of ligands for important receptors provides localized nitric oxide release, as would linkage to oligonucleotides capable of site-specific interactions with target sequences in a nucleic acid. Other proteins, peptides, polypeptides, nucleic acids and polysaccharides can be similarly utilized. U.S. Pat. No. 5,405,919 (Keefer et al.) and U.S. Pat. No. 5,632,981 (Saavedra et al.), hereby incorporated in their entireties by reference, disclose similar compounds and manufactures useful in the preparation of the diazeniumdiolates.

By way of illustration, an $O^2$-arylated piperazine diazeniumdiolate can be covalently attached to a polypeptide containing the IKVAV recognition sequence, which is important in tumor cell chemotaxis. Through retention of both the capacity to regenerate NO as an anti-adhesive agent and the affinity of the IKVAV sequence for tumor cells and/or sites in the vascular and lymphatic systems, where the tumor cells tend to attach, metastasis can be reduced or even prevented. Further, the aryl moiety can be chosen such that it provides additional antitumor cell activity. Substitutions at the $N^4$ position of piperazine can be used to link the glycosylated diazeniumdiolate to peptides, polypeptides, proteins, polysaccharides and nucleotides.

It is contemplated that the diazeniumdiolates of the present invention can be used to coat prostheses, stents, and medical implants, such as breast implants, prior to surgical connection to the body as a means of reducing the risk of solid state carcinogenesis associated therewith. Additionally, the prostheses and implants can be manufactured using a diazeniumdiolate as an integral component of the starting materials. Medical devices incorporating a diazeniumdiolate provide an invaluable two-pronged approach to the treatment of many biological disorders, providing useful medical structures that also advantageously provide local release of NO.

Compositions

As is well-known in the art, nitric oxide and compounds comprising $N_2O_2^-$ functional groups can have a wide range of utilities, in part because of the multifaceted role of nitric oxide in bioregulatory processes. Accordingly, the present invention also provides a composition, including a pharmaceutical composition, comprising a present inventive diazeniumdiolate. Preferably, the pharmaceutical composition additionally comprises a pharmaceutically acceptable carrier.

One skilled in the art will appreciate that suitable methods of administering the diazeniumdiolate compositions of the present invention to an animal, such as a mammal, are available, and, although more than one route can be used to administer a particular composition, a particular route can provide a more immediate and more effective reaction than another route. Pharmaceutically acceptable carriers are also well-known to those who are skilled in the art. The choice of carrier will be determined, in part, both by the particular composition and by the particular method used to administer the composition. Accordingly, there is a wide variety of suitable formulations of the pharmaceutical compositions of the present invention.

Formulations suitable for oral administration can consist of (a) liquid solutions, such as an effective amount of the diazeniumdiolate dissolved in diluents, such as water or saline, (b) capsules, sachets or- tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The diazeniumdiolates of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous solutions, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compositions employed (taking into consideration, at least, the rate of NO evolution, the extent of NO evolution, and the bioactivity of the decomposition products derived from the diazeniumdiolates) and the condition of the animal, as well as the body weight of the animal to be treated. The size of the dose also will be determined by the existence, nature, and extent of any adverse side effects that might accompany the administration of a particular composition. A suitable dosage for internal administration is 0.01 to 100 mg/kg per day. A preferred dosage is 0.01 to 35 mg/kg per day. A more preferred dosage is 0.05 to 5 mg/kg per day. A suitable concentration of $O^2$-aryl diazeniumdiolates in pharmaceutical compositions for topical administration is 0.05 to 15% (by weight). A preferred concentration is from 0.02 to 5%. A more preferred concentration is from 0.1 to 3%.

Methods of Use

In view of the above, the present invention provides methods of using a present inventive diazeniumdiolate. In one embodiment, a method of treating an animal, such as a mammal, with a biological disorder treatable with nitric oxide, is provided. The method comprises administering to the animal, e.g., the mammal, an amount of an diazeniumdiolate in accordance with the present invention sufficient to treat the biological disorder in the animal. In this embodiment, "biological disorder" can be any biological disorder, including a biological disorder due to a genetic defect or infection with an infectious agent, such as a virus, bacterium or parasite, as long as the disorder is treatable with nitric oxide.

In another embodiment of a method of use, a method is provided for treating an animal, such as a mammal, for infection with, for example, a virus, a bacterium, or a parasite (e.g., leishmania). The method comprises administering to the animal, e.g., the mammal, an amount of a diazeniumdiolate sufficient to treat the infection in the animal.

In one aspect of this embodiment of the invention, a method is provided for treating an animal, such as a mammal, for infection with, for example, a virus, such as a retrovirus, in particular HIV, more particularly HIV-1, a bacterium, such as a Gram-positive bacterium, or a parasite, such as Giardia, any one of which comprises a zinc finger protein that can be inactivated by an $O^2$-aryl diazeniumdiolate. By "zinc finger protein" is meant a protein comprising a short amino acid domain containing cysteines alone or cysteine and histidine ligands, both of which coordinate with zinc and interact with nucleic acids (South and Summers, "Zinc Fingers," Chapter 7, In: Adv. Inorg. Biochem. Ser. 8, pp. 199–248 (1990), which is hereby incorporated by reference in its entirety, including the content of all references cited therein). By "inactivated" is meant partial or complete loss of activity of the zinc finger protein to be inactivated. Such inactivation should not result in inactivation of biologically important zinc finger proteins in the animal, itself, to such an extent as to compromise unduly the health and well-being of the animal. The method comprises administering to the animal, e.g., the mammal, an amount of an $O^2$-aryl diazeniumdiolate sufficient to inactivate the zinc finger protein in said infectious agent so as to treat the infection in the animal.

The above-described method also can be adapted as a means of treating a plant, plant cell or tissue culture thereof for infection with an infectious agent, such as a virus, e.g., tobacco streak virus (TSV) or alfalfa mosaic virus (AIMV) (South and Summers (1990), supra; and Sehnke et al., *Virology* 168: 48 (1989)).

The methods described herein are useful against zinc fingers comprising the motif C—X2—C—X4—H—X4—C (see, e.g., Wain-Hobson et al., *Cell* 40(1): 9–17 (1985)), in which "C" represents cysteine, "H" represents histidine, "X" represents any amino acid, and the numbers "2" and "4" represent the number of "X" amino acids. Such a motif is characteristic of retroviruses, in particular the gag protein of retroviruses. Accordingly, the methods herein are useful against retroviruses, such as HIV, and, in particular, HIV-1 (Rice et al., *Nature Medicine* 3(3): 341–345 (1997); and Rice et al., *Reviews in Medical Virology* 6: 187–199 (1986)), which comprises nucleocapsid p7 proteins (NCp7 proteins) that include two zinc binding domains. Actual and/or potential zinc fingers also have been identified in, among others, the gene products of the EIA genomic region of adenoviruses, the large T antigens from simian virus 40 (SV40) and polyoma viruses, the UvrA protein in *E. coli* (Culp et al., *PNAS USA* 85: 6450 (1988)), murine leukemia virus (MuLV-F; Green et al., *PNAS USA* 86: 4047. (1989)), and bacteriophage proteins (Berg, *Science* 232: 484 (1986)), such as gene 32 protein (G32P) from bacteriophage T4 (Giedroc et al., *Biochemistry* 28: 2410 (1989)). Such proteins can be isolated in accordance with methods known in the art (see references cited in South and Summers (1990), supra), and the $O^2$-aryl diazeniumdiolates, which can inactivate such zinc finger proteins, can be identified in accordance, for example, with the zinc finger assay described herein and in Rice et al., *J. Med. Chem.* 39: 3606–3616 (1996).

To the extent that steroid hormone receptors comprise zinc fingers with motifs comprising 4 or 5 cysteines, an $O^2$-aryl diazeniumdiolate can be used to modulate steroid hormone activity in an animal, such as a mammal. Accordingly, the present invention also provides a method of modulating steroid hormone activity in an animal, such as a mammal, which is in need of modulation of steroid hormone activity and which comprises a steroid hormone receptor protein comprising a zinc finger that can be inactivated by an $O^2$-aryl diazeniumdiolate. The method comprises administering to the animal, e.g., the mammal, an amount of an $O^2$-aryl diazeniumdiolate sufficient to inactivate the steroid hormone receptor protein so as to modulate steroid hormone activity in the animal.

In yet another embodiment, a method for treating an animal, such as a mammal, for cancer and metastasis thereof is provided. The method comprises administering to the animal, e.g., the mammal, an amount of diazeniumdiolate sufficient to prevent the growth or metastasis of the cancer in the animal.

In one aspect of this embodiment, a method for treating an animal, such as a mammal, for cancer is provided, wherein the cancer is due, at least in part, directly or indirectly, to the activity of a zinc finger protein that can be inactivated by an $O^2$-aryl diazeniumdiolate. The method comprises administering to the animal, e.g., the mammal, an amount of $O^2$-aryl diazeniumdiolate sufficient to inactivate the zinc finger protein so as to treat the cancer in the animal (Rice et al., *PNAS* 89: 7703–7707 (1992)), i.e., prevent the growth or metastasis of the cancer in the animal.

In still yet another embodiment, a method is provided for treating an animal, such as a mammal, for cancer, wherein the cancer is resistant to treatment with a chemotherapeutic agent (see, e.g., Kelley et al., *Biochem. J.* 304: 843–848 (1994)), in particular a DNA damaging agent, such as an alkylating agent or an oxidizing agent, due, for example, to the action of an enzyme that adversely affects the activity of the chemotherapeutic agent. The method comprises administering to the animal, e.g., the mammal, an amount of an $O^2$-aryl diazeniumdiolate sufficient to render the cancer in the animal susceptible to treatment with the chemotherapeutic agent. Accordingly, such a method can be used as an adjunct therapy to chemotherapy as needed.

For example, certain $O^2$-aryl diazeniumdiolates can be synthesized to fit into the active site of glutathione S-transferase, specifically isoenzyme π (see, e.g., Ji et al., *Biochemistry* 32(49): 12949–12954 (1993); and Ji et al., *Biochemistry* 36: 9690–9702 (1997)). Accordingly, inversible consumption or glutathione from the active site of glutathione S-transferase-7 with an $O^2$-aryl diazeniumdiolate could prevent the enzyme from detoxifying a variety of xenobiotic compounds, such as chemotherapeutic drugs, especially alkylating agents, such as chlorambucil, melphalan and hepsulfam, and other DNA-damaging agents, such as agents that induce electrophilic attack or oxidization, by enzymatic conjugation of the compound with glutathione (see, e.g., Morgan et al., *Cancer Chemother. Pharmacol.* 37: 363–370 (1996)). This method also has applicability to screening drug-resistant cancer cell lines in vitro.

In another embodiment, a method is provided for treating an inanimate object for the presence of a potentially infectious virus, bacterium, or parasite. The method comprises contacting the inanimate object with an amount of a present inventive diazeniumdiolate sufficient to reduce the presence of the potentially infectious virus, bacterium or parasite. By "potentially infectious" is meant the capability of infecting an animal, such as a mammal.

In one aspect of this embodiment, a method is provided for reducing on an inanimate object the presence of a potentially infectious agent, such as a virus, a bacterium, or a parasite, any one of which comprises a zinc finger protein that can be inactivated by an $O^2$-aryl diazeniumdiolate. The method comprises contacting the inanimate object with an amount of an $O^2$-aryl diazeniumdiolate sufficient to inactivate the zinc finger protein so as to reduce the presence of the potentially infectious agent, e.g., virus, bacterium or parasite, on the inanimate object. By "potentially infectious" is meant the capability of infecting an animal, such as a mammal, directly or indirectly.

EXAMPLES

The following examples further illustrate the present invention and, of course, should not be construed as in any way limiting its scope. With respect to the following examples, NO was obtained from Matheson Gas Products (Montgomeryville, Pa.), β- and α-glycosidases and porcine liver esterase were obtained from Sigma Chemical Co. (St. Louis, Mo.), polyurethane (Tecoflex) was obtained from Thermedics Inc. (Woburn, Mass.), and glucose and mannose were obtained from Aldrich Chemical Co. (Milwaukee, Wis.). Proton NMR spectra were recorded with a 300 MHz Varian Unity Plus or a Varian XL-200 NMR spectrometer. Spectra were obtained in deuterochloroform for covalent compounds and in $D_2O$ for salts. Chemical shifts are reported in parts per million (ppm) downfield from TMS. Low and high resolution mass spectral (MS) measurements were carried out on a VG-Micromass Model 7070 spectrometer. Unless otherwise indicated, MS data were collected in the electron impact mode with sample introduction via direct probe. Ultraviolet (UV) spectra were run as solutions in water or 0.01 M NaOH on an HP 8451A Diode Array spectrophotometer. Glutathione S-transferase kinetics were monitored by measuring the change in UV absorbance at 380 nm with a Beckman DU 640 spectrophotometer. Chemiluminescence measurements were done on a Thermal Energy Analyzer Model 502A instrument (Thermedics, Inc., Woburn, Mass.). Elemental analyses were performed by Atlantic Microlab Inc.

EXAMPLE 1

This Example illustrates the preparation of $O^2$-(2,4-dinitrophenyl) 1-(N,N-diethylamino)diazen-1-ium-1,2-diolate.

A solution of 1.67 g (11 mmol) of sodium diethylaminodiazeniumdiolate in 20 ml of 5% aqueous sodium bicarbonate was cooled to 0° C. under nitrogen. A solution of 1.3 ml (0.01 mol) of 2,4-dinitrofluorobenzene in 10 ml of t-butyl alcohol was added slowly. A precipitate formed upon addition. The mixture was allowed to warm up to room temperature gradually, then stirred overnight. The product was extracted with dichloromethane and subsequently washed with cold dilute hydrochloric acid followed by sodium bicarbonate solution. The organic layer was dried over sodium sulfate, filtered through a layer of magnesium sulfate, and evaporated under vacuum to give 1.3 g of a red oil, which crystallized on standing. Recrystallization from ethanol gave yellow-orange needles: m.p. 76–7° C.; NMR δ 1.25 (t, 6H), 3.58 (q, 4H), 7.68 (d, 1H), 8.44 (m, 2H), 8.89 (m, 1H) ; UV (ethanol) $\lambda_{max}$ (ε) 218 (17.4 $mM^{-1}$ $cm^{1-}$) and 302 (15.6 $mM^{-1}$ $cm^{-1}$) nm; MS, exact mass, calculated for $C_{10}H_{13}N_5O_6$: (M+) 299.0865; measured $M^+$ 299.08658. Analysis, C, H, N, calculated for: $C_{10}H_{13}N_5O_6$: C 40.13%, H 4.35%, N 23.41%. Found: C 40.21%, H 4.43%, N 23.37%.

EXAMPLE 2

This Example illustrates the regeneration of the anionic diazeniumdiolate from its $O^2$-aryl substituted form ($O^2$-(2, 4-dinitrophenyl) 1-(N,N-diethyamino)diazen-1-ium-1,2-diolate).

A solution of 85 mg (0.28 mmol) of $O^2$-(2,4-dinitrophenyl) 1-(N,N-diethylamino)diazen-1-ium-1,2-diolate, prepared as in Example 1, in 1 ml of ether was cooled to −4° C. and treated with 1 ml of diethylamine. The solution was kept at −4° C. for 1 hr, giving a precipitate. The solid was collected by filtration. The filtrate was concentrated and analyzed by NMR; the residue proved to be identical to an authentic sample of 2,4-dinitro-N,N-diethylaniline. The precipitate was washed with petroleum ether and dried under $N_2$ to give 5.4 mg of product having $\lambda_{max}$ 250 nm; NMR ($D_2O$) δ 0.96 (t, 6H), 1.28(t, 6H), 2.94 (q, 4H), 3.08 (q, 4H). This product proved to be identical to an authentic sample of diethylammonium 1-(N,N-diethylamino)diazen-1-ium-1,2-diolate.

EXAMPLE 3

This Example illustrates the chemical cleavage of the $O^2$-aryl bond of an $O^2$-aryl diazeniumdiolate mediated by sodium methoxide.

A solution of 16 mg (0.064 mmol) of $O^2$-(2,4-dinitrophenyl) 1-(N,N-diethylamino)diazen-1-ium-1,2-diolate in 1 ml of ether was treated with 29 μl of 25% sodium methoxide in methanol (0.14 mmol) and allowed to stand at −4° C. for 2 hr. The solid precipitate was collected by filtration, washed with ether and dried under vacuum to yield 4 mg of a solid identical to an authentic sample of 1-(N,N-diethylamino)diazen-1-ium-1,2-diolate sodium salt.

EXAMPLE 4

This Example illustrates the kinetics of reaction of $O^2$-(2,4-dinitrophenyl) 1-(N,N-diethylamino)diazen-1-ium-1,2-diolate with sodium methoxide in methanol. The kinetics of this reaction show the rate of conversion of $O^2$-(2,4-dinitrophenyl) 1-(N,N-diethylamino)diazen-1-ium-1,2-diolate to 1-(N,N-diethylamino)diazen-1-ium-1,2-diolate ion in alkaline or nucleophilic environments.

An excess of NaOMe was used in the reactions; aliquots were collected at intervals and quenched with 0.1 N HCl in methanol. The disappearance of $O^2$(2,4-dinitrophenyl) 1-(N, N-diethylamino)diazen-1-ium-1,2-diolate, monitored by HPLC, was found to fit the first-order rate equation. This was determined by plotting log[$O^2$-(2,4-dinitrophenyl) 1-(N, N-diethylamino)diazen-1-ium-1,2-diolate] vs. time to find $k_{obs}$, at four different concentrations of NaOMe. Similarly, the second-order rate constant (7.87 $M^{-1}$ $min^{-1}$) was determined by plotting log kobs Vs. log[NaOMe].

EXAMPLE 5

This Example illustrates the preparation of $O^2$-(2,4-dinitrophenyl) 1-(N-isopropylamino)diazen-1-ium-1,2-diolate.

A solution of 84 mg (0.597 mmol) of sodium 1-(N-isopropylamino)diazen-1-ium-1,2-diolate in 1 ml of 5% sodium bicarbonate was cooled to 0° C. and 69 mg (0.55 mmol) of 2,4-dinitrofluorobenzene was added. The ice bath was removed, the mixture was allowed to stir at room temperature overnight, and then the mixture was extracted with dichloromethane. The extract was dried over sodium sulfate, filtered and evaporated in vacuo to give 86 mg of a film, which crystallized on standing: m.p. 92–93° C. NMR δ 1.39 (d, 6H), 3.99 (septet, 1H), 6.93 (d, 1 H), 8.27 (dd, 1H), 8.5 (b, 1H), 9.15 (d, 1H).

EXAMPLE 6

This Example illustrates the synthesis of pyrrolidinium 1-[pyrrolidin-1-yl]diazen-1-ium-1,2-diolate.

A solution of 36 g (0.507 mol) of pyrrolidine in 50 ml of ether and 25 ml of acetonitrile was placed in a 500 ml Parr bottle, degassed and charged with 40 psi of nitric oxide. The reactor was cooled to −80° C. The pressure was maintained at 40 psi. After 4 hr, the pressure was released, and the crystalline product was collected by filtration in a fritted glass funnel and then washed with cold ether under an atmosphere of nitrogen. The material was dried in a vacuum desiccator at 1 mm Hg and 25° C. for 3 hr to give 23 g (45%) of white needles: m.p. 68 70° C. Analysis C,H,N: Calculated for $C_8H18N_4O_2$: C 47.51%, H 8.97%, N 27.70%; Found, C 47.62%, H 9.04%, N 27.46%.

The pyrrolidinium salt was converted to the more stable sodium salt for subsequent $O^2$-arylations by treatment with 10 N NaOH to promote cation exchange. It was then flooded with ether. The product was collected by filtration.

EXAMPLE 7

This Example gives an alternate method of preparing the sodium salt of the 1-(pyrrolidin-1-yl)diazen-1-ium1,2-diolate presented in Example 6.

A solution of 28.2 g (0.397 mol) of pyrrolidine in 100 ml of acetonitrile and 100 ml of ether was mixed with 94 ml (0.4 mol) of 25% sodium methoxide in methanol. The resulting solution was flushed with nitrogen then charged with 40 psi of NO and stirred at room temperature for two days forming a thick precipitate. (The precipitate had begun to form within 1 hr of exposure to NO.) The pressure was released and the product was collected by filtration. The product was washed with ether and dried under vacuum to give 32.1 g (54%) of a white powder: UV (0.01 N NaOH) $\lambda_{max}$ (ϵ), 252 nm (8.84 mM$^{-1}$ cm$^{-1}$); $t_{1/2}$ 8.5 sec at 25° C. and 2.8 sec at 37° C. in pH 7.4 phosphate buffer; NMR ($D_2O$) δ 1.91 (m, 4H), 3.22 (m, 4H).

EXAMPLE 8

This Example illustrates the preparation of $O^2$-(2,4-dinitrophenyl) 1-(pyrrolidin-1-yl)diazen-1-ium-1,2-diolate.

A solution of 556 mg (3.63 mmol) of sodium 1(pyrrolidin-1-yl)diazen-1-ium-1,2-diolate in 10 ml of 5% aqueous sodium bicarbonate was cooled to 0° C. A solution of 456 μl (3.63 mmol) of 2,4-dinitrofluorobenzene in 2 ml of t-butyl alcohol was added and the resulting mixture was stirred at room temperature overnight. The yellow-orange precipitate was collected by filtration, washed with water, and dried to give 758 mg of product, which was recrystallized from ethanol: m.p. 94–95° C.; NMR, δ 2.04 (m, 4H), 3.35 (m, 4H), 6.90 (d, 1H), 8.20 (dd, 1H), 8.67 (d, 1H); MS, m/z(%), 297 (M$^+$, 1), 220 (100), 237 (30), 190 (94), 180 (15), 162 (10), 149 (26), 130 (20), 100 (95), 70 (24), 63 (35), 56 (18). Exact Mass: calculated for $C_{10}H_{11}N_5O_6$ (M$^+$)297.0708; measured 297.0709.

EXAMPLE 9

This Example illustrates the preparation of sodium 1-[(4-ethoxycarbonyl)piperazin-1-yl]diazen-1-ium-1,2-diolate.

A solution of 20 g (0.126 mol) of N-carboethoxypiperazine in 60 ml of methanol was placed in a Parr bottle. The solution was treated with 27.4 ml (0.126 mol) of 25% sodium methoxide in methanol; the system was evacuated, charged with 40 psi of nitric oxide and kept at 25° C. for 48 hr. The white crystalline product was collected by filtration and washed with cold methanol as well as with copious amounts of ether. The product was dried under vacuum to give a 14.5 g (48%) yield of sodium 1-[(4-ethoxycarbonyl)piperazin-1-yl]diazen-1-ium-1,2-diolate: m.p. 184–5° C.; UV (0.01 N NaOH) $\lambda_{max}$ (ϵ) 252 nm (10.4 mM$^{-1}$ cm$^{-1}$); NMR ($D_2O$) δ 1.25 (t, 3H), 2.15 (q, 2H) 3.11 (m, 4H), 3.68 (m, 4H). Anal calcd. for $C_6H_{13}N_4O_4Na$: C 35.00%, H 5.42%, N 23.33%, Na 9.58%. Found: C 34.87%, H 5.53%, N 23.26%, Na 9.69%.

The half-life of this compound at pH 7 and 25° C. was assessed at 5 min. This measurement was based on the loss of the 252 nm chromophore in the ultraviolet spectrum.

EXAMPLE 10

This Example illustrates the preparation of $O^2$-(2,4-dinitrophenyl) 1-[(4-ethoxycarbonyl)piperazin-1-yl]diazen-1-ium-1,2-diolate.

A solution of 1.073 g (0.0045 mol) of sodium 1-[(4-ethoxycarbonyl)piperazin-1-yl]diazen-1-ium-1,2-diolate in 10 ml of 5% sodium bicarbonate was cooled at 0° C. under nitrogen. A partial solution of 0.89 ml (0.0044 mol) of 2,4-dinitrofluorobenzene in 10 ml of t-butyl alcohol was added. A precipitate formed upon addition; the mixture was allowed to stir at room temperature for 4 hr. The product was extracted with dichloromethane. The extracts were washed with water, dried over sodium sulfate and filtered through a layer of anhydrous magnesium sulfate. Evaporation of the solvent gave an orange glass which crystallized on standing. The product was recrystallized from ethanol:dichloromethane to give 1.3 g (76%) of analytically pure material: m.p. 140–141° C.; NMR δ 1.32 (t, 3H), 3.63 (m, 4H), 3.74 (m, 4H), 4.19 (q, 2H), 7.66 (d, 1H), 8.48 (q, 1H), 8.88 (d, 1H); UV ($H_2O$) $\lambda_{max}$ (ϵ) 210 nm (13.3 mM$^{-1}$ cm$^{-1}$), 300 nm (12 mM$^{-1}$ cm$^{-1}$). Anal calcd. for $C_{13}H_{16}N_6O_8$: C 40.61%, H 4.20%, N 21.87%; Found: C 40.74%, H 4.13%, N 21.98%.

EXAMPLE 11

This Example illustrates the preparation of $O^2$-(2-chloropyrimidin-4-yl) 1-(N,N-diethylamino)diazen-1-ium-1,2-diolate.

A solution of 600 mg (4 mmol) of 2,4-dichloropyrimidine in 2 ml of dimethylsulfoxide and 5 ml of tetrahydrofuran was added via syringe to a slurry of 678 mg (4.37 mmol) of sodium 1-(N,N-diethylamino)diazen-1-ium-1,2-diolate in 5 ml of tetrahydrofuran at room temperature under nitrogen and the resulting mixture was stirred for 72 hr. Five (5) ml of ether was added to the mixture. After washing with water, the organic layer was dried over sodium sulfate, filtered through a layer of magnesium sulfate, and evaporated to give 679 mg of an oil which crystallized at −20° C. This material was recrystallized from ether-petroleum ether: m.p. 37–38° C.; NMR δ 1.25 (t, 6H), 3.56 (q, 4H), 7.00 (d, 1H), 8.50 (d,1H); UV, $\lambda_{max}$ (ϵ) 268 nm (9.3 mM$^{-1}$ cm$^{-1}$). Analysis C, H, N: Calculated for $C_8H_{12}N_5O_2Cl$: 39.11%, H 4.92%, N 28.51%, Cl 14.43%; Found: C 38.96%, H 4.96%, N 28.35%, Cl 14.60%.

EXAMPLE 12

This Example illustrates the preparation $O^2$-(2-chloropyrimidin-1-yl) 1-[(4-ethoxycarbonyl)piperazin-1-yl]diazen-1-ium-1,2-diolate.

A solution of 262 mg (1.76 mmol) of 2,4-dichloropyrimidine in 3 ml of dimethylsulfoxide was added to a slurry of 424 mg (1.76 mmol) of sodium 1-[(4-ethoxycarbonyl)piperazin-1-yl]diazen-1-ium-1,2-diolate in 10 ml of tetrahydrofuran at room temperature under nitrogen and stirred for 72 hr. The resulting homogeneous solution was treated with 100 ml of water. The precipitate was collected by filtration and dried under vacuum to give 300 mg of product: m.p. 136–137° C.; NMR δ 1.29 (t, 3H), 3.69 (m, 4H), 3.71 (m, 4H), 4.18 (q, 2 H), 6. 99 (d, 1 H), 8.52 (d, 1 H); (UV) $\lambda_{max}$ (ε) 270 nm (4.1 mM$^{-1}$ cm$^{-1}$).

This compound undergoes nucleophilic substitution with methoxide to displace the chlorine atom at the C2 position and the diazeniumdiolate at the C4 position to give 2,4-dimethoxypyrimidine.

EXAMPLE 13

This Example describes the synthesis of the following compounds:

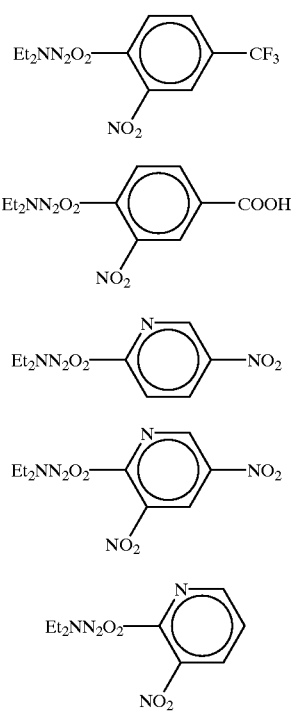

General synthesis of compounds 1 through 5: A 1 M solution of sodium 1-(N,N-diethylamino)diazen-1-ium-1,2-diolate in dimethylsulfoxide was stirred at 5° C. under nitrogen. A 1 M solution containing 0.95 molar equivalents of the arylating agent in tetrahydrofuran was injected through a septum. The reaction mixture was allowed to warm up to room temperature, stirred overnight, quenched with ice-water and extracted with ether. The ether was washed with water, dried over sodium sulfate, filtered through a layer of maganesium sulfate and concentrated on a rotary evaporator. The methods of purification varied with each preparation and are described with the individual compounds below. (Note: Compounds 1 through 5 are selected products from O$^2$-aryl compound libraries built using solution phase synthetic methods in parallel fashion). NMR spectra were run in CDCl$_3$.

O$^2$-(2-Nitro-4-trifluoromethylphenyl) 1-(N,N-diethylamino) diazen-1-ium-1,2-diolate, 1: Arylation was carried out with 4-fluoro-3-nitrobenzotrifluoride. Purification of the product was carried out on preparative HPLC using a 1 inch C-18 column eluted with 20% aqueous acetonitrile with a solvent gradient to 50% acetonitrile:50% water. A 42% yield of product was obtained as an oil: NMR δ 1.23 (t, 6H), 3.50 (q,4 H), 7.66 (d, 1 H), 7.82 (d, 1 H), 8.28 (s, 1 H).

O$^2$-(2-Nitro-4-carboxylatophenyl) 1-(N,N-diethylamino) diazen-1-ium-1,2-diolate, 2: 4-Fluoro-3-nitrobenzoic acid was used in this preparation. Purification of the product was carried out on a Biotage Flash 40 system with a 4.0×15.0 cm KP-Sil column. The system was eluted with 5:1 dichloromethane:ethyl acetate at 15 psi of air at a rate of elution of 25 ml/min to give a 22% yield of product: mp 115–6° C.; NMR δ 1.22 (t, 6 H), 3.33 (q, 4 H), 7.06 (d, 1 H), 8.03 (dd, 1 H), 8.37 (m, 1 H).

O$^2$-(5-Nitropyrid-2-yl)1-(N,N-diethyl)diazen-1-ium-1,2-diolate, 3: The product of reaction with 2-bromo-5-nitropyridine was recrystallized from ether:ethanol to give pure 3. in 62% yield: mp 77–8° C.; NMR δ 1.24 (t, 6 H), 3.53 (q, 4 H), 7.21 (dd, 1 H), 8.52 (dd, 1 H), 9.17 (dd, 1 H). Analysis C,H,N: Calculated for C$_9$H$_{13}$N$_5$O$_4$: C 42.35%, H 5.13%, N 27.44%, Found: C 42.46%, H 5.14%, N 27.52%.

O$^2$(3,5-Dinitropyrid-2-yl)1-(N,N-diethyl)diazen-1-ium-1,2-diolate, 4: Anylation was effected with 2-chloro-3,5-dinitropyridine as described in the general procedure. The crude product was recrystallized from ether:petroleum ether to give 4 in 33% yield: mp 56–7° C.; NMR δ 1.28 (t 6 H), 3.57 (q,4 H), 8.81 (d, 1 H), 9.10 (d, 1 H).

O$^2$-(3-Nitropyrid-2-yl)1-(N,N-diethyl)diazen-1-ium-1,2-diolate, 5: 2-Chloro-3-nitropyridine was used in this reaction. The crude product was purified on a Flash 40 system using a 4.0×7.0 cm KP-Sil column eluted with 100% dichloromethane to give a 52% yield of product as a viscous oil: NMR δ 1.25 (t, 6 H), 3.55 (q, 4 H), 7.26 (m, 1 H), 8.48 (m, 2 H).

EXAMPLE 14

This Example illustrates the preparation of O$^2$-vinyl 1-[(2-carboxylato)pyrrolidin-1-yl]diazen-1-ium-1,2-diolate (V-PROLI/NO).

To 3.56 g (9.2 mmol) of O$^2$-(2-bromoethyl) 1-[(2-carboxylato)pyrrolidin-1-yl]diazen-1-ium-1,2-diolate 2-bromoethyl ester was added 10 ml of 10 N sodium hydroxide solution.

The two-phase mixture was stirred at 25° C., whereupon the compound gradually dissolved in the aqueous layer. After stirring overnight, the UV of the reaction mixture exhibited an absorption maximum at 266 nm (starting material absorbed at 252 nm), indicating the formation of a vinyl group.

The solution was cooled to 0° C. and carefully acidified to pH 4 by the slow addition of 10% hydrochloric acid. Care must be taken to keep the solution cold while acid is added. The acidic solution was extracted with ethyl acetate, dried over sodium sulfate and filtered through a layer of magnesium sulfate. Evaporation of the solvent gave 1.4 g of an oil. Purification was carried out on a Flash 40 System (Biotage) using a 4.0×7.0 cm KP-Sil column and 2:1 ethyl acetate-:cyclohexane as the eluant:ir (film) 3163, 2987, 1734, 1630, 1490 cm$^{-1}$; NMR (CDCl$_3$) δ 2.06–2.3 (m,4H), 3.62 (m,2H), 4.47 (q,1H), 4.77 (ABq, 1H), 5.02 (ABq, 1H), 6.75 (q,1H); UV $\lambda_{max}$ (ε) 266 nm(6.3 mM$^{-1}$ cm$^{-1}$); MS,m/z (%) 201 (M$^+$, 5), 176(10), 150(49), 145(27), 114(9) 99(45), 70(99.9), 69(57), 68(45).

EXAMPLE 15

This Example illustrates the regeneration of NO from O$^2$-(2,4-dinitrophenyl) 1-(N,N-diethylamino)diazen-1-ium-1,2-diolate in the presence, but not the absence, of glutathione.

A solution containing 1 mM glutathione (GSH) in 10 mM phosphate buffer was degassed by purging with argon for 10 min, whereupon a 3 ml aliquot was mixed with 3 μl of a dioxane solution that was 2 mM in $O^2$-(2,4-dinitrophenyl) 1-(N,N-diethylamino)diazen-1-ium-1,2-diolate. NO release was monitored by chemiluminescence while the mixture was held at 37° C. After a brief lag time, peak nitric oxide generation was observed at approximately 15 minutes after the reaction was initiated and continued at readily detectable levels for approximately 100 minutes. Total NO generation during the first 112 min was approximately 9 nmol. Assuming that 2 nmol of NO is generated per mol of O2-(2,4-dinitrophenyl) 1-(N,N-diethylamino)diazen-1-ium-1,2-diolate, this 9 nmol corresponds to roughly 75% of the theoretical yield.

When the reaction was repeated as above but with exclusion of the GSH, no NO generation was observed. The nucleophilic glutathione reacted with the $O^2$-(2,4-dinitrophenyl) 1-(N,N-diethylamino)diazen-1-ium-1,2-diolate to produce NO according to the equation shown below.

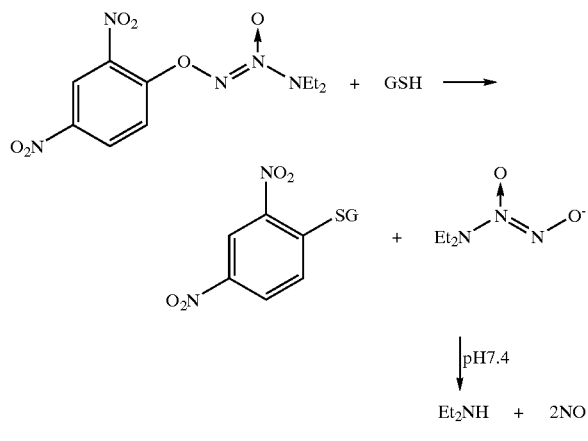

This example is illustrative of the ability of some of the $O^2$-aryl diazeniumdiolate compounds of the present invention to undergo nucleophilic substitution by nucleophilic side-chains of amino acids such as cysteine, which are often found in the active sites of enzymes. The result of such nucleophilic substitution is the generation of an aryl derivative of the displacing amino acid residue and a diazeniumdiolate capable of producing NO, through a predictable, first-order reaction.

$O^2$-(2,4-Dinitrophenyl) 1-(N,N-diethylamino)diazen-1-ium-1,2-diolate and glutathione were also assayed in the presence and absence of glutathione S-transferase. Assays were conducted in a thermostated cell compartment at 25° C., using 0.1 M phosphate buffer at pH 7.4, with a final volume of 3 ml. The concentration of the enzyme was 0.7 μg/ml, whereas that of glutathione was 1.4 mM. The concentration of diazeniumdiolate was varied from 50–100 μM. Using the integrated form of the Henri-Michaelis-Menten equation, $K_m$ was found to be 46.3 μM and $V_{max}$ was found to be 0.89 μM min$^{-1}$.

EXAMPLE 16

This Example illustrates a route of synthesis which is useful in the production of diazeniumdiolated nucleotides, nucleosides, and nucleic acids and further illustrates a route to synthesis of $O^2$-aryl diazeniumdiolates, which comprises converting an amino group to a diazonium group, followed by reaction of the diazonium group with a diazeniumdiolate.

2'-Deoxycytidine is reacted with nitric oxide in the presence of a suitable 1-electron oxidant which results in the conversion of the amino group of the cytidine into a diazonium group while reducing the oxidant and producing hydroxide ion. The resulting diazotized (i.e., diazonium derivatized) pyrimidine is then reacted with 1-(N,N-diethylamino)diazen-1-ium-1,2-diolate ion, as described in the previous examples, to generate a diazeniumdiolated 2'-deoxyuridine derivative. This diazeniumdiolated 2'-deoxyuridine derivative can be reacted with strong nucleophiles (e.g., hydroxide ions). This will result in the regeneration of 1-(N,N-diethylamino)diazen-1-ium-1,2-diolate ion plus 2'-deoxyuridine. This regenerated 1-(N,N-diethylamino)diazen-1-ium-1,2-diolate ion will generate NO in a predictable, first-order reaction. This Example demonstrates a basis for a mechanism that is suitable for targeting nitric oxide to a particular site of a mammalian body, so that the specificity of NO action can be increased.

EXAMPLE 17

This example demonstrates the ability of an $O^2$-aryl diazeniumdiolate to inactivate a zinc finger protein by zinc ejection.

Samples of recombinant nucleocapsid protein p7 (p7NC) from HIV-1 (L. O. Arthur, AIDS Vaccine Program, NCI-FCRDC, Frederick, Md.) were prepared at μg/ml in 10 mM sodium phosphate buffer (pH=7.0) and treated with 25 μmol of an $O^2$-aryl diazeniumdiolate in a total volume of 1.0 ml. At various time intervals, as shown in FIG. 1, which is a graph of Trp37 fluorescence (RFU) versus time (min), the samples were diluted 1/10 in 10 mM sodium phosphate buffer (pH=7.0) to prevent introduction of any artifactual quenching effects and the fluorescence intensity of the tryptophan residue (Trp37) in the C-terminal zinc finger of p7NC in each sample was determined as previously described (Rice et al., *Int. Antiviral News* 3: 87–89 (1995)). The excitation and emission wavelengths utilized with a Shimadzu RF5000 spectrofluorimeter were 280 and 351 nm, respectively. The results are shown in FIG. 1, in which ○ represents the negative control, i.e., no drug, □ represents the positive control, i.e., 642151 (see Rice et al. (1997), supra), ■ represents the compound of Example 1 (LK1), ♦ represents the compound of Example 8 (LK2), ▲ represents the compound of Example 5 (LK3), ● represents the compound of Example 10 (LK4), and x represents the compound of Example 11 (LK5). The results indicate that an $O^2$-aryl diazeniumdiolate can eject zinc from a zinc finger protein.

EXAMPLE 18

This example demonstrates the anti-HIV activity of $O^2$-aryl diazeniumdiolates.

The tumor cell line of T4 lymphocytes designated CEM-SS was grown in a synthetic medium with fetal bovine serum (Rice et al., *Advances in Pharmacol.* 33: 389–438 (1995)). $O^2$-aryl diazeniumdiolates were administered to HIV-1-infected and uninfected CEM-SS cells at concentrations ranging from $10^{-3.5}$ to $10^{-7.0}$ M in accordance with the XTT-based cell viability assay of the National Cancer Institute (see, e.g., Rice et al. (1995), supra).

After exposure of CEM-SS cells to the compounds, the percentage of T-cell viability was assessed. The viability of HIV-1-infected CEM-SS cells, which were contacted with a subtoxic concentration of any one of the above-described $O^2$-aryl diazeniumdiolates, was substantially increased in comparison to untreated cells. Compounds 1–3 from Example 13 were especially effective.

EXAMPLE 19

This example describes the preparation of disodium 1-[(2-carboxylato)pyrrolidin-1-yl]diazen-1-ium-1,2-diolate.

A solution of 10 g (0.087 mol) of L-proline in 39 ml (0.18 mol) of 25% sodium methoxide in methanol, 20 ml of methanol and 40 ml of ether was degassed and exposed to 40 psi of nitric oxide for 20 hr. The pressure was released and the solid residue was collected by filtration, washed with ether and dried under vacuum to give 17 g of a white solid: mp 250° C. (dec.); UV (0.01 N NaOH) $\lambda_{max}$ ($\epsilon$) 252 nm (8.4 mM$^{-1}$ cm$^{-1}$); NMR (D$_2$O) $\delta$ 1.71 (m, 1H), 1.91 (m, 2H), 2.27 (m, 1H), 3.27–3.43 (m, 2H), 4.04 (m, 1H) (a methanol singlet at 3.34 is also observed); $^{13}$C NMR, 24.45 ppm, 30.97, 48.73 (methanol), 54.95, 67.70, 182.75.

Anal. C,H,N: Calculated for $C_5H_7N_3O_4Na_2 \cdot CH_3OH$, C 28.69%, H 4.41%, N 16.73%, Na 18.30%; Found C 28.65%, H 3.99%, N 16.74%, Na 18.04%.

EXAMPLE 20

This example describes the preparation of $O^2$-methyl 1-[(2-carboxylato)pyrrolidin-1-yl)diazen-1-ium-1,2-diolate methyl ester.

Disodium 1-[(2-carboxylato)pyrrolidin-1-yl]diazen-1-ium-1,2-diolate (methanol solvate, FW 251; 6.8 g; 0.027 mol) was placed in a 300 ml 3-neck flask and cooled to –20° C. Cold methanol (–20° C.; 200 ml) was added to the solid while stirring to give a homogeneous solution, which was cooled further to –35° C. A solution of 9.5 ml (0.1 mol) of dimethylsulfate in 25 ml of ether was added dropwise over a 15 min period. The reaction mixture was then allowed to warm to room temperature gradually and stirred for an additional 4 hr. The progress of the reaction was monitored on silica gel TLC using 10:1 dichloromethane:ethyl acetate as the eluant. The reaction mixture was filtered, the methanol was removed on a rotary evaporator, and the residue was extracted with dichloromethane. The solution was washed with aqueous sodium bicarbonate, dried over sodium sulfate and filtered through a layer of magnesium sulfate. Evaporation of the solvent gave an oil, which crystallized on standing. Recrystallization from ether:petroleum ether gave 945 mg (18%) of an analytically pure sample: mp 62–63° C.; UV (0.01 N NaOH), $\lambda_{max}$ ($\epsilon$) 252 nm (6.79 mM$^{-1}$ cm$^{-1}$); NMR $\delta$ 2.05 (m, 3H), 2.30 (m, 1H), 3.65 (m, 1H), 3.75 (s, 3H), 3.83 (m, 1H), 3.96 (s, 3H), 4.55 (m, 1H); MS m/z (%) 203 (M$^+$, 6), 188 (20), 58 (35), 120 (22), 99 (100), 95 (34), 69 (36), 59 (24); exact mass calculated for $C_7H_{13}N_3O_4$ (M$^+$) 203.0906, found (M$^+$) 203.0906.

Anal. C,H,N: Calculated for $C_7H_{13}N_3O_4$, C 41.38%, H 6.45%, N 20.68%: Found C 41.48%, H 6.43%, N 20.59%.

EXAMPLE 21

This example describes the preparation of $O^2$-(N,N-dimethylsulfamoyl) 1-[(2-carboxylato)pyrrolidin-1-yl] diazen-1-ium-1,2-diolate.

A solution of 1.08 ml (0.01 mol) of N,N-dimethylsulfamoyl chloride in 5 ml of tetrahydrofuran was added dropwise to a cold (0° C.) solution of 1.57 g (0.0062 mol) of disodium 1-[(2-carboxylato)pyrrolidin-1-yl]diazen-1-ium-1,2-diolate in 25 ml of 0.1 N NaOH in saline solution. The reaction mixture was allowed to warm up to room temperature and stirred overnight. The aqueous layer was extracted with dichloromethane and the organic layer was dried over anhydrous sodium sulfate. The aqueous layer showed no significant UV absorption after extraction and, thus, indicated that the extraction products were devoid of diazeniumdiolate. The organic layer was filtered through a layer of magnesium sulfate and the solvent was removed on a rotary evaporator to give 989 mg of a pale yellow oil, which was chromatographed on silica gel using 5:1 dichloromethane:ethyl acetate as the eluant. The fractions containing the desired product were combined and concentrated under vacuum to give a solid, which was recrystallized from ether-petroleum ether: mp 97–98° C.; UV (0.01 N NaOH) $\lambda_{max}$ ($\epsilon$) 266 nm (8.05 mM$^{-1}$ cm$^{-1}$); NMR $\delta$ 2.16 (m, 3H), 2.40 (m, 1H), 3.01 (s, 6H), 3.83 (m, 1H), 3.94 (m, 1H), 4.69 (q, 1H), 6.80 (b, 1H).

Anal. C,H,N,S: Calculated for $C_7H_{14}N_4SO_6$, C 29.79%, H 5.00%, N 19.85%, S 11.36%: Found C 29.93%, H 5.09%, N 19.76%, S 11.27%.

EXAMPLE 22

This example describes the preparation of $O^2$-methoxymethyl 1-[(2-carboxylato)pyrrolidin-1-yl] diazen-1-ium-1,2-diolate methoxymethyl ester.

A slurry of 485 mg (1.93 mmol) of disodium 1-[(2-carboxylato)pyrrolidin-1-yl]diazen-1-ium-1,2-diolate in 20 ml of anhydrous tetrahydrofuran was cooled to 0° C. under a nitrogen atmosphere. Triethylamine (0.5 ml) was added to the cold solution followed by the slow addition of 360 mg (4.45 mmol) of chloromethylmethyl ether and a subsequent dropwise addition of 0.5 ml of methanol. The solution was then stirred in the cold for 1.5 hr. The reaction mixture was allowed to warm up to room temperature and stirred under nitrogen for an additional 1.5 hr. The reaction was quenched with crushed ice, whereupon the solvent was removed on a rotary evaporator and the residue was extracted with dichloromethane. The organic phase was washed with water, dried over sodium sulfate, filtered through magnesium sulfate and evaporated in vacuo to give 330 mg of a yellow oil, which was purified on a silica gel column with 5:1 dichloromethane:ethyl acetate as the eluant: UV (H$_2$O) $\lambda_{max}$ ($\epsilon$) 250 nm (8.58 mM$^{-1}$ cm$^{-1}$); NMR $\delta$ 2.09 (m, 3H), 2.35 (m, 1H), 3.48 (s, H), 3.71 (m, 2H), 3.90 (m, 1H), 4.61 (dd, 1H), 5.17 (ab q, 2H), 5.31 (ab q, 2H).

Anal. C,H,N: Calculated for $C_9H_{17}N_3O_6$: C 41.06%, H 6.51%, N 15.96 %: Found C 40.87%, H 6.53%, N 15.76%.

EXAMPLE 23

This example describes the preparation of $O^2$-(2-bromoethyl) 1-((2-carboxylato)pyrrolidin-1-yl]diazen-1-ium-1,2-diolate 2-bromoethyl ester.

A solution of 20 ml (0.28 mol) of bromoethanol in 50 ml of dichloromethane was cooled to 0° C. and 11.25 ml (0.28 mol) of sulfuryl chloride in 50 ml of dichloromethane was added dropwise to the solution. The resulting solution was kept at 4° C. for 72 hr. The solution was washed with cold 10% NaOH until the washings tested distinctly basic. The organic layer was dried over sodium sulfate, filtered through a layer of magnesium sulfate and concentrated on a rotary evaporator. The resulting crude product (2-bromoethoxysulfonyl chloride, $BrCH_2CH_2OSO_2Cl$) was vacuum-distilled to give 35 g (56%) of a colorless oil: bp 73–75° C. at 1.5 mmHg; NMR δ 3.64 (t, 2H), 4.752 (t, 2H); MS m/z (%) 221 ($M^+$, 1), 143 (10), 129 (25), 106 (100), 93 (62). Analysis C,H,N,S,X: Calculated for $C_2H_4SO_3ClBr$: C 10.75%, H 1.80%, S 14.35%, total halogen as Br 71.52% and as Cl 31.72%; Found: C 10.82% H 1.80%, S 14.35%, total halogen as Br 71.63% and as Cl 31.78%.

Disodium 1-[(2-carboxylato)pyrrolidin-1-yl]diazen-1-ium-1,2-diolate (4.86 g; 0.0194 mol) was placed in a 100 ml round-bottom flask, together with 2.2 g of anhydrous sodium carbonate. The flask was immersed in a dry ice-acetonitrile bath (at −40° C.) and 50 ml of cold (−20° C) ethanol was added. Then the mixture was stirred and allowed to stabilize at −40° C. under an atmosphere of nitrogen. To the cold slurry was added, via a syringe, 9.45 g (0.0422 mol) of 2-bromoethoxysulfonyl chloride over a period of 10 min. After stirring for 2 hr, the reaction mixture was allowed to warm to 15° C. and stirred for an additional 2 hr. The reaction mixture was poured into 250 ml of ice-water and extracted with dichloromethane. The organic layer was washed with aqueous sodium bisulfite solution, dried over sodium sulfate and filtered through a layer of magnesium sulfate, whereupon the solvent was removed on a rotary evaporator. The crude product was chromatographed on a silica gel column using 1:1 cyclohexane:ethyl acetate as the eluant to give 2.7 g (36%) of a pale yellow oil: NMR δ 2.11 (m, 3H), 2.35 (m, 1H), 3.55 (m, 4H), 3.68 (m, 1H), 3.86 (m, 1H), 4.46 (m, 4H), 4.59 (m, 1H); UV ($H^2O$) $\lambda_{max}$ (ε) 252 nm (6.6 $mM^{-1}$ $cm^{-1}$).

EXAMPLE 24

This example describes the preparation of $O^2$-[S-acetyl-(2-mercaptoethyl)]1-[(2-carboxylato)pyrrolidin-1-yl]diazen-1-ium-1,2-diolate [S-acetyl-(2-mercaptoethyl)]ester.

1,8-Diazabicyclo[5.4.0]undec-7-ene (DBU) (1.03 g; 0.0068 mol) was added to a solution of 1.33 g (0.0034 mol) of $O^2$-(2-bromoethyl) 1-[(2-carboxylato)pyrrolidin-1-yl]diazen-1-ium-1,2-diolate 2-bromoethyl ester in 35 ml of tetrahydrofuran and the resulting solution was stirred at room temperature under nitrogen. Two equivalents of thiolacetic acid (0.479 ml, 0.0068 mol) were added and the mixture was stirred at room temperature for 2 hr. The mixture was filtered and the solid residue was washed with ether. The filtrate was evaporated to dryness under reduced pressure and the residue was extracted with methylene chloride. The organic solution was subsequently washed with ice-cold 5 N HCl, sodium bicarbonate solution and water. The solution was dried over sodium sulfate, filtered through a layer of magnesium sulfate and evaporated in vacuo to give 710 mg of a yellow oil. Chromatography was carried out on a silica gel column eluted with 1:1 cyclohexane:ethyl acetate: UV ($H_2O$) $\lambda_{max}$ (ε) 232 nm (7.0 $mM^{-1}$ $cm^{-1}$); NMR δ 2.09 (m, 3H), 2.36 (m, 1H), 2.38 (s, 6H), 3.09 (m, 4H), 3.78 (m, 2H), 4.27 (m, 4H), 4.55 (m, 1H).

EXAMPLE 25

This example describes the determination of the halflife of the compound produced in Example 24 in the absence and presence of porcine liver esterase at 25° C. and pH 7.4.

A 0.009 M ethanolic stock solution of $O^2$-[S-acetyl-(2-mercaptoethyl)]1-[(2-carboxylato)pyrrolidin-1-yl]diazen-1-ium-1,2-diolate [S-acetyl-(2-mercapto-ethyl)]ester was prepared. The decay of this compound was monitored at 25° C. as $1.5 \times 10^{-4}$ M solutions in a 4 ml quartz cuvette containing 3 ml of phosphate buffer (pH 7.4) and 50 ml of stock solution. The decay of the 232 nm chromophore was monitored on the ultraviolet spectrophotometer. The halflife was estimated as 3.2 hr.

A second set of experiments was carried out using the above parameters to measure the decay after addition of 5 ml of porcine liver esterase suspension. The half-life for the esterase reaction was 8 min at 25° C.

EXAMPLE 26

This example describes the preparation of a nitric oxide-releasing polymer-blend of $O^2$-[S-acetyl-(2-mercaptoethyl)] 1-[(2-carboxylato)pyrrolidin-1-yl]diazen-1-ium-1,2-diolate [S-acetyl-(2-mercaptoethyl)]ester.

A solution of 50 mg (0.132 mmol) of $O^2$-[S-acetyl-(2-mercaptoethyl)]1-[(2-carboxylato)pyrrolidin-1-yl]diazen-1-ium-1,2-diolate [S-acetyl-(2-mercaptoethyl)]ester in 1 ml of tetrahydrofuran was dissolved in a solution of 498 mg of polyurethane in 10 ml of tetrahydrofuran. The homogeneous lacquer was concentrated under a stream of dry nitrogen followed by further drying under high vacuum to give a solid, which contained 0.091 mg (0.24 mmol) of $O^2$-[S-acetyl-(2-mercaptoethyl)]1-[(2-carboxylato)pyrrolidin-1-yl] diazen-1-ium-1,2-diolate [S-acetyl-(2-mercaptoethyl)]ester per mg of polymer composite. Rates of NO release were measured as a function of time after immersing a 32 mg aliquot of the diazeniumdiolate in 2 ml of phosphate buffer, pH 7.4, at 37° C., with a chemiluminescence detector. A set of experiments was carried out in plain buffer, while another set was done in the presence of porcine liver esterase. A very small amount of NO was released in the absence of enzyme over a 200 hr period, while a significant rate of NO production was observed when the enzyme was present in the buffer. This indicates that as the diazeniumdiolate oozes out of the polymer composite, it is hydrolyzed by the enzyme with further cleavage to NO.

EXAMPLE 27

This example describes the introduction of the nitric oxide-releasing $O^2$-[S-acetyl-(2-mercaptoethyl)]1-[(2-carboxylato)pyrrolidin-1-yl]diazen-1-ium-1,2-diolate [S-acetyl-(2-mercaptoethyl)]ester into β-cyclodextrin.

β-Cyclodextrin (228 mg, 0.201 mmol) was mixed with 2 ml of water and heated to 65° C. to give a homogeneous solution. To the warm solution was added 76 mg (0.201 mmol) of $O^2$-[S-acetyl-(2-mercaptoethyl)]1-[(2-carboxylato)pyrrolidin-1-yl]diazen-1-ium-1,2-diolate

[S-acetyl-(2-mercaptoethyl)]ester. Upon mixing, a white precipitate formed. The mixture was allowed to cool to room temperature and the product was collected by filtration, washed with water, and dried under vacuum to give 170 mg of product. An aqueous solution containing 33 mg of the $O^2$-[S-acetyl-(2-mercaptoethyl)]1-[(2-carboxylato) pyrrolidin-1-yl]diazen-1-ium-1,2-diolate [S-acetyl-(2-mercaptoethyl)]ester: β-cyclodextrin mixture exhibited an absorbance maximum at 232 nm and a molar absorptivity (E) of 10.8 $mM^{-1}cm^{-1}$. Rates of NO release were measured as a function of time after immersing a 13 mg aliquot of the encapsulated material in 4 ml of phosphate buffer, pH 7.4, at 37° C., with a chemiluminescence detector. A set of experiments was carried out in plain buffer, while another set was done in the presence of porcine liver esterase. A very small amount of NO was released in the absence of enzyme over a 400 hr period while a significant rate of NO production was observed when the enzyme was present in the buffer.

EXAMPLE 28

This example describes a general procedure for the preparation of $O^2$-glycosylated diazeniumdiolates. 2,3,4,6-Tetraacetyl-α-D-glucopyranosyl bromide (acetobromoglucose) was prepared as described in Redemann et al., *Org. Syn. Coll.* Vol. III: 11–14 (1955). 2,3,4,6-Tetraacetyl-α-D-mannopyranosyl bromide (acetobromomannose) was prepared as described in Levene et al., *J. Biol. Chem.* 90: 247–250 (1931). Then, a slurry of 1 eq of a diazeniumdiolate in dimethylsulfoxide (DMSO) (0.5 mmol solid/1 ml of DMSO) was stirred with 0.03 eq of silver oxide at room temperature under nitrogen. A 0.5 M solution of 1.2 eq of acetobromomannose or acetobromoglucose in DMSO was injected dropwise and the mixture was stirred for three days. The resulting homogeneous solution was poured into 100 ml of ice-water and extracted with ether. The ether layer was washed with water, dried over sodium sulfate and treated with charcoal. The solution was filtered through magnesium sulfate, concentrated on a rotary evaporator, and dried under vacuum. The glucose derivatives were purified by recrystallization, while the glassy mannose adducts required column chromatography.

EXAMPLE 29

This example describes the preparation of sodium 1-(N,N-diethylamino)diazen-1-ium-1,2-diolate ("DEA/NO").

A solution of 119 g (1.63 mol) of diethylamine in 100 ml of 1:1 ether:acetonitrile was placed in a 500 ml Parr bottle. The solution was degassed, charged with 40 psi of nitric oxide, and allowed to stand at room temperature overnight. The pressure was released and the crystalline product was collected by filtration and dried under nitrogen to give 13 g of diethylammonium 1-(N,N-diethylamino)diazen-1-ium-1,2-diolate. The salt was treated with 10 ml of 10 M sodium hydroxide solution and the resulting paste was treated with 200 ml of ether to give the sodium salt. The sodium salt ("DEA/NO") was collected by vacuum filtration, washed with ether, and dried under vacuum to give 7.1 g of product: UV (in 0.01 N NaOH) $\lambda_{max}$ (ε) 250 (6.88 $mM^{-1}cm^{-1}$); NMR ($D_2O$) δ 0.96 (t, 3 H), 2.94 (q, 2 H); in DMSO-$d_6$ δ 0.84 (t, 3 H) and 2.75 (q, 2 H).

EXAMPLE 30

This example describes the preparation of $O^2$-(2,3,4,6-tetra-O-acetyl-α-D-glucopyranosyl) 1-(N,N-diethylamino) diazen-1-ium-1,2-diolate.

DEA/NO (2.98 g; 0.019 mol) in DMSO was reacted with acetobromoglucose (6.9 g; 0.017 mol) as described in the general procedure of Example 28. The product was recrystallized from petroleum ether to give 5.7 g (72%) 108 mg of a crystalline solid: mp 107–108° C.; UV $\lambda_{max}$ (ε) 228 nm (6.92 $mM^{-1}cm^{-1}$); NMR δ 1.11 (t, 6 H, J=7.11), 2.02 (s, 3 H), 2.03 (s, 3 H), 2.04 (s, 3 H), 2.07 (s, 3 H), 3.21 (q, 4 H, J=7.12), 3.81 (m, 1 H), 4.20 (m, 2 H), 5.14 (m, 1 H), 5.33 (m, 3 H). Anal. Calcd for $C_{18}H_{29}N_3O_{11}$: C, 46.65; H, 6.31; N, 9.07. Found: C, 46.73; H, 6.26; N, 9.01.

EXAMPLE 31

This example describes the deacylation of $O^2$-(2,3,4,6-tetra-O-acetyl-α-D-glucopyranosyl) 1-(N,N-diethylamino) diazen-1-ium-1,2-diolate(from Example 30).

A solution of 253 mg (0.55 mmol) of the above compound in 5 ml of methanol was stirred with 10 μl of 25% methanolic sodium methoxide. The progress of the reaction was monitored by TLC using 5:1 $CH_2Cl_2$:ethyl acetate. The reaction was complete within 1 h at 25° C.

Dowex-50W-$H^+$ resin (1 g) was added to the stirring methanolic solution. The mixture was filtered to remove the resin, and the methanolic solution was evaporated under vacuum to give 122 mg (75%) of $O^2$-glucopyranosyl 1-(N,N-diethylamino)diazen-1-ium-1,2-diolate: UV $\lambda_{max}$ (ε) 228 nm (6.4 $mM^{-1}$ $cm^{-1}$); NMR ($CDCl_3$) δ 1.08 (t,6H), 3.23 (9,4H), 5.59 (m,4H), 3.88 (m,2H), 5.29 (m,1H).

Surprisingly, the deacetylated product cleaved to the 1-(N,N-diethylamino)diazen-1-ium-1,2-diolate (DEA/NO) anion, then to NO, only extremely slowly at pH 3, despite its acetal-like structure. Even more surprisingly, the cleavage proceeded extremely rapidly at pH 13.

EXAMPLE 32

This example describes the preparation of sodium 1-[(1-ethoxycarbonyl)piperazin-4-yl]diazen-1-ium-1,2-diolate.

A solution of 20 g (0.126 mol) of carboethoxy piperazine in 60 ml of methanol was placed in a Parr bottle. The solution was treated with 27.4 ml (0.126 mol) of 25% sodium methoxide in methanol. The system was evacuated, charged with 40 psi of nitric oxide and kept at 25° C. for 48 hr. The white crystalline product was collected by filtration and washed with cold methanol as well as with copious amounts of ether. The product was dried under vacuum to give 14.5 g (48% yield) of sodium 1-[(1-ethoxycarbonyl) piperazin-4-yl]diazen-1-ium-1,2-diolate: mp: 184–185° C.; UV (0.01 N NaOH) $\lambda_{max}$ (ε) 252 nm (10 $mM^{-1}$ $cm^{-1}$); NMR ($D_2O$) δ 1.25 (t, 3 H), 3.11 (m, 2 H), 3.68(m, 2 H), 2.15 (q, 2 H). Anal calcd. for $C_6H_{13}N_4O_4Na$: C 35.00%, H 5.42%, N 23.33%, Na 9.58%. Found: C 34.87%, H 5.53%, N 23.26%, Na 9.69%. The half-life of this compound at pH 7 and 25° C. was estimated as 5 min. This measurement was based on the loss of the 252 nm chromophore in the ultraviolet spectrum.

EXAMPLE 33

This example describes the preparation of $O^2$-(glucopyranos-2-yl) 1-[(1-ethoxycarbonyl)piperazin-4-yl] diazen-1-ium-1,2-diolate tetraacetate ester.

Acetobromoglucose (2.055 g; 0.005 mol) and 1.11 g (0.00466 mol) of sodium 1-[(1-ethoxycarbonyl)piperazin-4- yl]diazen-1-ium-1,2-diolate were reacted as described above to give 624 mg (25%) of $O^2$-(glucopyranos-2-yl) 1-[(1-ethoxycarbonyl)piperazin-4-yl]diazen-1-ium-1,2-diolate tetraacetate ester: UV $\lambda_{max}$ ($\epsilon$) 228 nm (7.20 mM$^{-1}$ cm$^{-1}$); NMR $\delta$ 1.26 (t, 3 H), 2.02 (s, 3H), 2.03 (s, 3H), 2.04 (s, 3 H), 2.09 (s, 3 H), 3.46 (m, 4H), 3.68 (m, 4 H), 3.82 (m, 1 H), 4.17 (q, 2 H), 4.25 (m, 3 H), 5.27 (m, 3 H).

EXAMPLE 34

This example describes the preparation of $O^2$-(mannopyranos-2-yl) 1-[(1-ethoxycarbonyl)piperazin-4-yl)] diazen-1-ium-1,2-diolate tetraacetate.

Acetobromomannose (10.2 g; 0.025 mol) and 5.28 g (0.022 mol) of sodium 1-[(1-ethoxycarbonyl)piperazin-4-yl] diazen-1-ium-1,2-diolate were reacted as described above to give 6.4 g (53%) of a glass: UV $\lambda_{max}$ ($\epsilon$) 238 nm (7.5 mM$^{-1}$ cm$^{-1}$) NMR $\delta$ 1.29 (t, 3 H), 2.01 (s, 3H), 2.05 (s, 3H), 2.11 (s, 3 H), 2.17 (s, 3 H), 3.13 (m, 1 H), 3.50 (m, 4 H), 3.78 (m, 5 H), 4.19 (q, 2 H), 4.27(m, 3 H), 5.28 (m, 3 H), 5.42 (m, 1H).

EXAMPLE 35

This example describes the preparation of an $O^2$-glycosylated diazeniumdiolate directed to a mannose-fucose receptor.

Bis-[2-(N-ethoxycarbonylamino)ethyl]amine: A three-neck flask equipped with two dropping funnels was immersed in an ice-water bath. DiethyLenetriamine (10.7 g, 0.104 mol) was placed in the cold flask and dissolved in 100 ml of 95% ethanol. To the cold solution was added 10 ml (0.205 mol) of ethylchloroformate, dropwise. A solution of 10.6 g (0.1 mol) of sodium carbonate in 100 ml of distilled water was added simultaneously with 10 ml (0.205 mol) of ethylchloroformate. The reaction mixture was allowed to stir at room temperature overnight. The ethanol was removed on a rotary evaporator and the aqueous portion was extracted with dichloromethane. The organic layer was washed with water, then extracted with 5% hydrochloric acid. The organic layer containing the neutral products was separated and set aside. The aqueous layer was washed with dichloromethane and made basic with sodium hydroxide. The product was extracted into dichloromethane, dried over sodium sulfate, filtered through magnesium sulfate and evaporated to give 4 g of a colorless oil: NMR (CDCl$_3$) $\delta$ 1.25 (t, 6H), 2.78 (m, 4H), 3.36 (m, 4H), 4.14 (q, 4H), 5,13 (b, 2H).
Sodium 1-[bis-{2-(N-ethoxycarbonylamino)ethyl}amino] diazen-1-ium-1,2-diolate: A solution of 2.6 g (0.011 mol) of bis-[2-(N-ethoxycarbonylamino)ethyl]amine in 20 ml of ether and 5 ml of methanol was placed in a 50 ml Parr bottle, treated with 2.4 ml (0.011 mol) of 25% methanolic sodium methoxide, degassed, cooled to –80° C. and charged with 50 psi of nitric oxide. A thick precipitate was observed after 3 hr of stirring. The mixture was exposed to NO for 24 hr, the pressure was released, and the product was collected by filtration. The solid was washed with ether and dried under vacuum to give 1.26 g (35%) of the diazeniumdiolate: mp 170–2° C.; UV $\lambda_{max}$ ($\epsilon$) 252 nm (7.6 mM$^{-1}$ cm$^{-1}$); NMR $\delta$ 1.24 (t, 6H), 3.19 (m, 8H), 4.11 (q, 4H).
$O^2$-(Mannos-2-yl) 1-[bis-{2-(N-ethoxycarbonylamino) ethyl}amino]diazen-1-ium-1,2-diolate tetraacetate: A partial solution of 251 mg (0.763 mmol) of sodium 1-[bis-{2-(N-ethoxycarbonylamino)ethyl}amino]diazen-1-ium-1,2-diolate in 2 ml of dimethylsulfoxide (DMSO) was cooled to 0° C. under nitrogen. To this was added 10 mg (0.06 mmol) of silver acetate, followed by the slow addition of 1 ml of a 0.82 M solution of acetobromomannose in tetrahydrofuran. The reaction mixture was allowed to stir at room temperature for 48 hr, poured over ice-water, and extracted with ether. The ether solution was dried over sodium sulfate, filtered through a layer of magnesium sulfate, and evaporated under vacuum to give 307 mg of an oil: UV $\lambda_{max}$ 240 nm.

$O^2$-(Mannos-2-yl)1-[bis(2-aminoethyl)amino]diazen-1-ium-1,2-diolate]:

A solution of 145 mg (0.23 mmol) of $O^2$-(mannos-2-yl) 1-[bis-{2-(N-ethoxycarbonylamino)ethyl}amino]diazen-1-ium-1,2-diolate tetraacetate in a mixture of 0.2 ml of 10 N NaOH, 2 ml of ethanol and 2 ml of water was heated at reflux for 15 hr. The solution was concentrated under vacuum and the remaining aqueous solution was extracted with dichloromethane. The aqueous solution was evaporated to dryness under vacuum. The residue was taken up in methanol, put through a 10 g, 60 cc prepacked C-18 column, and eluted with methanol. The fractions exhibiting an absorption maximum at 236 nm were combined and evaporated to give 32 mg of a white powder: NMR (CD$_3$OD) $\delta$ 2.74 (t, 4H), 3.02 (t, 4H), 3.74 (m, 4H), 4.2 (m, 3H); UV $\lambda_{max}$ 238 nm.

EXAMPLE 36

This example describes the preparation of a combinatorial library using disodium 1-(2-carboxylato)pyrrolidin-1-yl diazen-1-ium-1,2-diolate (PROLI/NO) as starting material.

The piperazine trityl resin 1, available from Calbiochem-Novabichem Int'l. (San Diego, Calif.), is treated with sulfuryl chloride to form the chlorosulfonamide 2. Reaction of this resin with PROLI/NO gives compound 3. The free carboxylic acid can be activated to 4 by reaction with dicyclohexyl carbodiimide (DCC) and N-hydroxysuccinimide. Nucleophilic addition of $R^{30}$XH (X=O, N, S) to the resin-bound diazeniumdiolate provides a potentially large library of compounds, 5, substituted at the carboxylato portion of the molecule. Base hydrolysis of 5 frees the anionic diazeniumdiolate 6 from the resin. This library, 6, may now be reacted with electrophiles $R^{31}$X to form new sets of compound having structure 7.

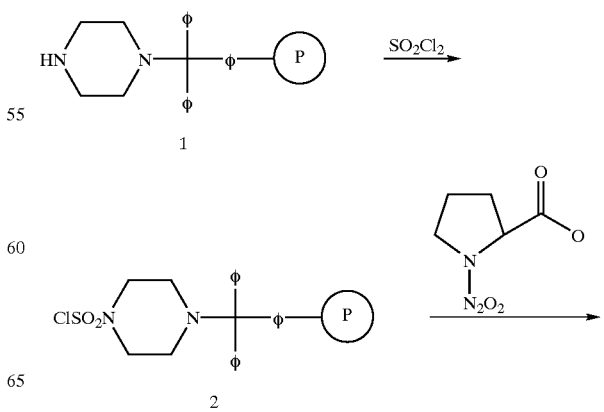

All publications, patents and patent applications, cited herein are hereby incorporated by reference to the same extent as if each publication were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. An $O^2$-substituted diazeniumdiolate having the formula $$X-N\rightarrow O$$
$$\|$$
$$N-O-Q$$
(I)

wherein X is selected from the group consisting of an amino, a polyamino, a $C_1$–$C_{24}$ aliphatic, a $C_6$–$C_{30}$ aryl, a $C_3$–$C_{30}$ heteroaromatic having 1 to 3 heteroatorms selected from the group consisting of oxygen, nitrogen and sulfur, a $C_3$–$C_{30}$ nonaromatic cyclic, and an oximyl, and Q is selected from the group consisting of an acridinyl, an anthracenyl, a benzimidazolyl, a benzisoxazolyl, a benzofuryl, a benzothienyl, a benzoxazolyl, a benzopyrazolyl, a benzothiazolyl, a carbazolyl, a chlorophyllyl, a cinnolyl, a furyl, an imidazolyl, an indolyl, an isobenzofuryl, an isoindolyl, an isoxazolyl, an isothiazolyl, an isoquinolyl, a naphthyl, an oxazolyl, a phenanthryl, a phenanthridinyl, a phenothiazinyl, a phenoxazinyl, a phenyl, a phthalimidyl, a phthalazinyl, a phthalocyaninyl, a pteridinyl, a purinyl, which isoptionally part of a nucleic acid, a ribosylpurinyl, a pyrazinyl, a pyrazolyl, a pyridazyl, a pyridyl, a pyrimidyl, which is optionally part of a nucleic acid, a ribosylpyrimidyl, a pyrrocolinyl, a pyrryl, a quinolyl, a quinoxalinyl, a quinazolinyl, a sydnonyl, a tetrazolyl, a thiazolyl, a thienyl, a thyroxinyl, a triazinyl, and a triazolyl, wherein a ring atom of Q is bonded to the $O^2$-oxygen, wherein X and Q are optionally substituted, with the proviso that, when Q is an imidazolyl, X is not an imidazolyl.

2. The diazeniumdiolate of claim 1, wherein Q is part of a vitamin.

3. The diazeniumdiolate of claim 1, wherein Q is part of a hormone.

4. The diazeniumdiolate of claim 1, wherein Q is a pyrimidyl, which, optionally, is part of a nucleic acid.

5. The diazeniumdiolate of claim 4, wherein Q is a ribosylpyrimidyl.

6. The diazeniumdiolate of claim 1, wherein Q is a purinyl, which, optionally, is part of a nucleic acid.

7. The compound of claim 6, wherein Q is a ribosylpurinyl.

8. The diazeniumdiolate of claim 1, wherein X is linked to the $N^1$ nitrogen through an atom other than a carbon atom.

9. The diazeniumdiolate of claim 1, wherein X is substituted with one or more moieties selected from the group consisting of —[N(NO)O$^-$], a halo, hydroxy, an alkylthio, an alkoxy, an aryloxy, an amino, cyano, a sulfonato, mercapto, nitro, a $C_1$–$C_{12}$ aliphatic, a $C_3$–$C_8$ cycloalkyl, a $C_3$–$C_8$ heterocyclic, a $C_2$–$C_{12}$ olefinic, benzyl, phenyl, benzylcarbonyl, phenylcarbonyl, glucosyl, ribosyl, glucosyl, mannosyl, deoxyribosyl, dextranyl, starch, glycogenyl, lactosyl, fucosyl, galactosyl, fructosyl, glucosaminyl, galactosaminyl, heparinyl, maltosyl, sucrosyl, sialyl, cellulose, phosphorylated pentosyl, polyphosphorylated pentosyl, phosphorylated hexosyl, polyphosphorylated hexosyl, phosphono, phosphato, and phosphato in which one or more oxygen atoms are independently replaced with S or $NR^1$, wherein $R^1$ is a $C_1$–$C_8$ aliphatic, a $C_3$–$C_8$ cycloalkyl, a $C_6$–$C_8$ aryl, or a $C_3$–$C_8$ heteroaromatic having 1 to 3 heteroatoms selected from the group consisting of oxygen, nitrogen and sulfur.

10. The diazeniumdiolate of claim 1, wherein Q is substituted with one or more moieties selected from the group consisting of X[N(O)NO]$^-$, wherein X is as defined in claim 1, halo, hydroxy, alkylthio, arylthio, alkoxy, aryloxy, amino, mono- or di-substituted amino, ammonio, substituted ammonio, nitroso, cyano, sulfonato, mercapto, nitro, oxo, a $C_1$–$C_{24}$ aliphatic, a $C_2$–$C_{12}$ olefinic, a $C_3$–$C_{24}$ cycloalkyl, a $C_3$–$C_{24}$ heterocyclic, benzyl, phenyl, substituted benzyl, substituted phenyl, benzylcarbonyl, phenylcarbonyl, glucosyl, ribosyl, glucosyl, mannosyl, deoxyribosyl, dextranyl, starch, glycogenyl, lactosyl, fucosyl, galactosyl, fructosyl, glucosaminyl, galactosaminyl, heparinyl, maltosyl, sucrosyl, sialyl, cellulose, phosphorylated pentosyl, polyphosphorylated pentosyl, phosphorylated hexosyl, polyphosphorylated hexosyl, substituted benzylcarbonyl, substituted phenylcarbonyl, phosphono, phosphato, and phosphato in which one or more oxygen atoms are independently replaced with S or $NR^1$, wherein $R^1$ is a $C_1$–$C_{10}$ aliphatic, a $C_3$–$C_{10}$ cycloalkyl, a $C_6$–$C_{10}$ aryl, or a $C_1$–$C_{10}$ heteroaromatic having 1 to 3 heteroatoms selected from the group consisting of oxygen, nitrogen and sulfur.

11. The diazeniumdiolate of claim 1, having the formula

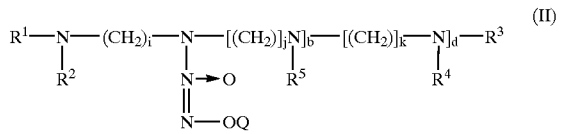
(II)

wherein b and d can be the same or different and may be zero or one, $R^1$, $R^2$, $R^3$, $R^4$, and $R^5$ are the same or different and are selected from the group consisting of hydrogen, $C_3$–$C_8$ cycloalkyl, $C_{1\text{-}12}$ straight or branched chain alkyl, benzyl, benzoyl, phthaloyl, acetyl, trifluoroacetyl, p-toluyl, t-butoxycarbonyl, or 2,2,2-trihalo-t-butoxycarbonyl, and i, j, and k are the same or different and are integers from 2 to 12.

12. The diazeniumdiolate of claim 1, having the formula

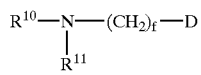

wherein D is

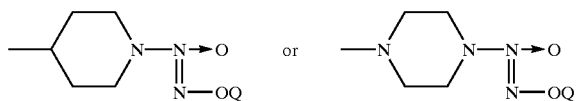

and wherein $R^{10}$ and $R^{11}$ are the same or different and are selected from the group consisting of hydrogen, $C_{3\text{-}8}$ cycloalkyl, $C_{1\text{-}12}$ straight or branched chain alkyl, benzyl, benzoyl, phthaloyl, acetyl, trifluoroacetyl, p-toluyl, t-butoxycarbonyl, and 2,2,2-trichloro-t-butoxycarbonyl, and f is an integer from 0 to 12.

13. The diazeniumdiolate of claim 1, having the formula:

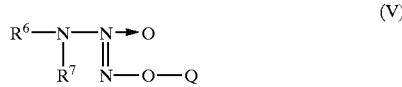
(V)

wherein $R^6$ and $R^7$ can be the same or different and are H, a $C_1$–$C_{12}$ straight chain alkyl, a $C_1$–$C_{12}$ alkoxy or acyloxy substituted straight chain alkyl, a $C_2$–$C_{12}$ hydroxy or halo substituted straight chain alkyl, a $C_3$–$C_{12}$ branched chain alkyl, a $C_3$–$C_{12}$ hydroxy, halo, alkoxy, or acyloxy substituted branched chain alkyl, a $C_2$–$C_{12}$ straight chain olefinic, or a $C_3$–$C_{12}$ branched chain olefinic, wherein $R^6$ and $R^7$ are optionally substituted with hydroxy, alkoxy, acyloxy, halo or benzyl; or $R^6$ and $R^7$ together with the nitrogen atom to which they are bonded form a heterocyclic ring selected from the group consisting of:

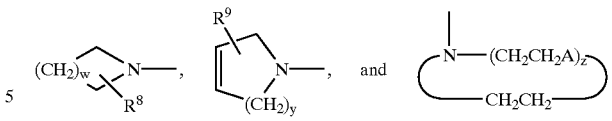

wherein A is N, O, or S, w is 1 to 12, y is 1 or 2, z is 1 to 5, $R^8$ is hydrogen, a $C_1$–$C_8$ straight chain alkyl, a $C_3$–$C_8$ branched chain alkyl, a $C_3$–$C_8$ cycloalkyl, a $C_6$–$C_{30}$ aryl, a $C_3$–$C_{30}$ heteroaromatic having 1 to 3 heteroatoms selected from the group consisting of oxygen, nitrogen and sulfur, and $R^9$ is hydrogen, a $C_1$–$C_6$ straight chain alkyl or a $C_3$–$C_6$ branched chain alkyl.

14. The diazeniumdiolate of claim 13, wherein $R^6$ is hydrogen.

15. The diazeniumdiolate of claim 13, wherein $R^6$ and $R^7$ are ethyl and Q is selected from the group consisting of:

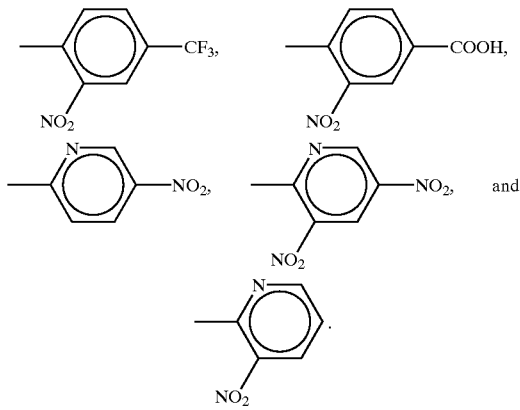

16. An $O^2$-substituted diazeniumdiolate having the formula

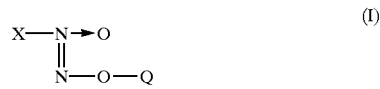
(I)

wherein X is an inorganic moiety that results in a compound of Formula (I) capable of disassociating under physiological conditions and Q is selected from the group consisting of an acridinyl, an anthracenyl, a benzimidazolyl, a benzisoxazolyl, a benzofuryl, a benzothienyl, a benzoxazolyl, a benzopyrazolyl, a benzothiazolyl, a carbazolyl, a chlorophyllyl, a cinnolyl, a furyl, an imidazolyl, an indolyl, an isobenzofuryl, an isoindolyl, an isoxazolyl, an isothiazolyl, an isoquinolyl, a naphthyl, an oxazolyl, a phenanthryl, a phenanthridinyl, a phenothiazinyl, a phenoxazinyl, a phenyl, a phthalimidyl, a phthalazinyl, a phthalocyaninyl, a pteridinyl, a purinyl, which is optionally part of a nucleic acid, a ribosylpurinyl, a pyrazinyl, a pyrazolyl, a pyridazyl, a pyridyl, a pyrimidyl, which is optionally part of a nucleic acid, a ribosylpyrimidyl, a pyrrocolinyl, a pyrryl, a quinolyl, a quinoxalinyl, a quinazolinyl, a sydnonyl, a tetrazolyl, a thiazolyl, a thienyl, a thyroxinyl, a triazinyl, and a triazolyl; wherein a ring atom of Q is bonded to the $O^2$-oxygen, wherein X and Q are optionally substituted.

17. The diazeniumdiolate of claim 16, wherein X is $^-$O— or $^-O_3$S—.

18. A composition comprising a diazeniumdiolate of claim 1 and a carrier.

19. The composition of claim 18, wherein the ring atom of Q bonded to said $O^2$-oxygen is carbon or nitrogen.

20. A composition comprising a diazeniumdiolate of claim 16, and a carrier.

21. The composition of claim 20, wherein the ring atom of Q bonded to said $O^2$-oxygen is carbon or nitrogen.

22. A method of treating or preventing a biological disorder in an animal, wherein said disorder is selected from the group consisting of angina, acute myocardial infarction, congestive heart failure, hypertension and metastasis, which method comprises administering to said animal an amount of a compound of claim 1 or a diazeniumdiolate of formula

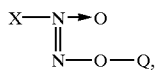

wherein X and Q are imidazoles, sufficient to treat or prevent the biological disorder in said animal.

23. The method of claim 22, wherein said biological disorder is due to hypertension.

24. The method of claim 22, wherein said biological disorder is due to acute myocardial infarction.

25. The method of claim 22, wherein said biological disorder is due to metastasis.

26. A method of treating or preventing a biological disorder in an animal, wherein said disorder is selected from the group consisting of angina, acute myocardial infarction, congestive heart failure, hypertension and metastasis, which method comprises administering to said animal an amount of a compound of claim 16 sufficient to treat or prevent the biological disorder in said animal.

27. A method of treating or preventing a biological disorder in a mammal, wherein said disorder is selected from the group consisting of angina, acute myocardial infarction, congestive heart failure, hypertension and metastasis, which method comprises administering to the animal a compound of claim 1 or a diazeniumdiolate of formula

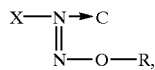

(Ia)

in which X and R are compounds comprising a pyranose ring or a furanose ring, wherein the compounds are attached to the $O^2$ of the diazeniumdiolate by the 2 position of the pyranose ring or the furanose ring, in an amount sufficient to treat or prevent the biological disorder.

28. The diazeniumdiolate of claim 16, wherein Q is part of a vitamin.

29. The diazeniumdiolate of claim 16, wherein Q is part of a hormone.

30. A method of treating an animal infected with an infectious agent comprising a zinc finger protein that can be inactivated by nitric oxide, the method comprising administering to said animal an amount of a compound of claim 1, 16 or a diazeniumdiolate of formula

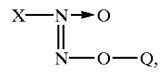

wherein X and Q are imidazoles, sufficient to inactivate the zinc finger protein in the infectious agent so as to treat the infection in the animal.

31. A method of treating an animal for cancer, wherein the cancer involves a zinc finger protein that can be inactivated by nitric oxide, the method comprising administering to the animal an amount of a compound of claim 1, 16 or a diazeniumdiolate of formula

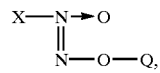

wherein X and Q are imidazoles, sufficient to inactivate the zinc finger protein so as to treat the cancer in said animal.

32. A method of treating an animal for cancer, wherein the cancer is resistant to treatment with a chemotherapeutic agent, the method comprising administering to the animal an amount of a compound of claim 1, 16 or a diazeniumdiolate of formula

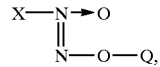

wherein X and Q are imidazoles, sufficient to render the cancer in the animal treatable with the chemotherapeutic agent.

33. A method of modulating steroid hormone activity in a mammal, wherein the mammal is in need of modulation of steroid hormone and wherein the animal has a steroid hormone receptor comprising a zinc finger protein which can be inactivated by nitric oxide, the method comprising administering to the animal an amount of a compound of claim 1, 16 or a diazeniumdiolate of formula.

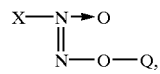

wherein X and Q are imidazoles, sufficient to inactivate the steroid hormone receptor protein so as to modulate steroid hormone activity in the mammal.

34. The method of claim 30, wherein the infectious agent is a virus.

35. The method of claim 34, wherein the virus is HIV.

36. The method of claim 30, wherein said infectious agent is a parasite.

37. The method of claim 36, wherein said parasite is Giardia.

38. The method of claim 32, wherein the chemotherapeutic agent is a DNA-damaging agent.

39. The method of claim 38, wherein the DNA-damaging agent is selected from the group consisting of an alkylating agent and an oxidizing agent.

* * * * *